(12) United States Patent
Flematti et al.

(10) Patent No.: US 7,576,213 B2
(45) Date of Patent: Aug. 18, 2009

(54) VINYLOGOUS 4H-PYRONES AND THEIR USE IN PROMOTING PLANT GROWTH

(75) Inventors: Gavin Ray Flematti, Cooloongup (AU); Emilio Luciano Ghisalberti, North Perth (AU); Kingsly Wayne Dixon, City Beach (AU); Robert Donald Trengove, Trigg (AU)

(73) Assignee: The University of Western Australia (AU)

( * ) Notice: Subject to any disclaimer, the term of this patent is extended or adjusted under 35 U.S.C. 154(b) by 46 days.

(21) Appl. No.: 11/471,163

(22) Filed: Jun. 19, 2006

(65) Prior Publication Data

US 2007/0105721 A1    May 10, 2007

Related U.S. Application Data

(63) Continuation of application No. PCT/AU2004/001824, filed on Dec. 22, 2004.

(51) Int. Cl.
*C07D 493/04* (2006.01)
*C07D 491/048* (2006.01)

(52) U.S. Cl. .................. 546/116; 549/23; 549/305; 549/306

(58) Field of Classification Search ................. 546/116; 549/23, 305, 306
See application file for complete search history.

(56) References Cited

OTHER PUBLICATIONS

Chem. Abstracts, Registry No. 343827-43-0, Jun. 28, 2001.*
Adkins and Peters (2001) Seed Science Research 11:213-222.
Adrianz et al. (2000) Analytical Letters 33(3):2793-2804.
Baldwin et al. (1994a) Journal of Chemical Ecology 20(9):2345-2371.
Baldwin and Morse (1994b) Journal of Chemical Ecology 20(9):2373-2391.
Baxter and Van Staden (1994a) Plant Growth Reglation 14:279-282.
Baxter et al. (1994b) Environmental and Experimental Botany 34(2):217-223.
Baxter et al. (1995) S. Afr. J. Bot. 61(5):275-277.
Blank and Young (1998) J. Range Manage. 51:577-583.
Boucher and Meets (2004) South African Journal of Botany 70(2):313-318.
Brown, N.A. (Mar. 1993) New Phytologist 123(3):575-583.
Brown, N.A. (Mar. 1993) Int. J. Wildland Fire 3(4):203-206.
Brown et al. (1993) Seed Sci & Tech. 21:573-580.
Brown et al. (1994) Plant Growth Regulation 15:93-100.
Brown et al. (Sep. 1994) Veld & Flora 72-73.
Brown and van Staden (1997) Plant Growth Regulation 22:115-124.
Brown and van Staden (1998) Seed Sci & Tech. 26:669-673.
Brown et al. (1998) S. Afr. J. Bot. 54(1):90-92.
Brown and Botha (Jun. 2002) Veld & Flora 88:58-59.
Brown and Botha (2004) South African Journal of Botany 70(4):559-581.
De Lange and Boucher (1990) S. Afr. J. Bot. 56(6):700-703.
Dixon et al. (1995) Oecologia 101:185-192.
Doherty and Cohen (2000) Seed Science Research 10:415-421.
Drewes et al. (1995) Plant Growth Regulation 16:205-209.
Egerton Warburton (Aug. 1998) 49(325):1317-1327.
Enright and Kintrup (2001) 26:132-141.
Flematti et al. (2001) Analytical Letters 34(12):2221-2225.
Flematti et al. (Aug. 13. 2004) Science 305:997.
Flematti et al. (2004) Plant and Soil 263:1-4.
Gardner et al. (2001) South African Journal of Botany 67:636-640.
Jager et al. (1996) Environmental and Experimental Botany 36(4):421-429.
Jager et al. (1996) Plant Growth Regulation 19:197-201.
Keeley et al (Jul. 1985) The Journal of Ecology 73(2):445-458.
Keeley and Pizzorno (Sep. 1986) American Journal of Botany 73(9):1289-1287.
Keeley and Bond (1997) Plant Ecology 133:153-167.
Keeley and Fotheringham (May 23, 1997) Science 276:1248-1250.
Keeley and Fotheringham (Oct. 1998) Ecology 79(7):2320-2336.
Keeley and Fotheringham (Feb. 1998) The Journal of Ecology 86(1):27-36.
Light and van Staden (2004) South African Journal of Botany 70(1):97-101.
Lloyd et al. (2000) Austral. Eclology 25:610-615.
Minorsky, P.V. (2002) Plant Physiol. 128:1167-1168.
Modi, A.T. (2004) South African Journal of Botany 70(1):16-23.
Perez-Fernandez and Rodriguez-Echeverria (Jan. 2003) Journal of Chemical Ecology 29(1):237-251.
Pierce et al. (1995) Oecologia 102:520-522.
Preston and Baldwin (Mar. 1999) Ecology 80(2):481-494.
Preston et al. (2004) Seed Science Research 14:73-79.
Read and Bellairs (1999) Aust. J. Bot. 47:563-576.
Read et al. (2000) Austral. Ecology 25:48-57
Roche et al. (Sep. 1994) Australian Horticulture :46-48.
Roche et al. (1997) Aust. J. Bot. 45:783-815.

(Continued)

*Primary Examiner*—Bernard Dentz
(74) *Attorney, Agent, or Firm*—Edwards Angell Palmer & Dodge LLP; Kathleen Williams

(57) ABSTRACT

A hitherto unknown class of chemical compounds, 2H-furo[2,3-c]pyran-2-ones including derivatives and analogues thereof are disclosed herein. Methods for making compounds within said class are disclosed herein and includes, without limitation, at least the intermediates employed in the generation of said compounds. The invention also relates to the use of vinylogous 4H-pyrones, including but not limited to the hitherto unknown 2H-furo[2,3-c]pyran-2-ones. Disclosed herein are methods comprising the step of exposing biological plant material to at least a compound of the invention to promoting bioactivity within said material. In another aspect in methods for promoting growth of plant material in, for example, smoke-responsive plant species by exposing said material to a compound of the invention are disclosed herein. More specifically, methods comprising the use of these compounds for promoting seed germination of a plant, for example, a smoke-responsive plant, are disclosed herein.

26 Claims, 9 Drawing Sheets

OTHER PUBLICATIONS

Rokich et al. (Jun. 2002) Restoration Ecology 10(2):185-194.
Senaratna et al. (1999) Plant Growth Regulation 28:95-99.
Strydom et al. (1996) Plant Growth Regulation 19:97-100.
Taylor and van Staden (1996) Plant Growth Regulation 18:165-168.
Thanos and Rundel (Apr. 1995) The Journal of Ecology 83(2):207-216.
Thomas and van Staden (1995) Plant Growth Regulation 17:195-198.
Thornton et al. (1999) Plant Growth Regulation 28:129-132
Tieu et al. (1999) Aust. J. Bot. 47:207-219.
Tieu et al. (2001) Annals of Botany 88:259-265.
Van Staden et al. (1995) Plant Growth Regulation 17:241-249.
Van Staden et al. (1995) Plant Growth Regulation 17:213-218.
Van Staden et al. (1995) S. Afr. J. Bot. 61(5):260-263.
Van Staden et al. (2000) Plant Species Biology 15:167-178.
Van Staden et al. (2004) South African Journal of Botany 70(4):654-659.
Went et al. (Jul. 1952) Ecology 33(3):351-364.
Wicklow, D.T. (Jan. 1997) Ecology 58(1):201-205.

* cited by examiner

US 7,576,213 B2

VINYLOGOUS 4H-PYRONES AND THEIR USE IN PROMOTING PLANT GROWTH

This application is a continuation of PCT/AU2004/001824, filed Dec. 22, 2004, which designated the U.S. and of AU 2003907066 filed Dec. 22, 2003.

FIELD OF THE INVENTION

The present invention relates to a class of chemical compounds known as vinylogous 4H-pyrones, including the previously unknown class of compounds, 2H-furo[2,3-c]pyran-2-ones, that exhibit bioactivity when in the presence of biological material such as plant species. It also includes methods for making compounds within said class and includes, without limitation, at least the intermediates employed in the generation of said compounds. It also provides methods for regulating growth of plant material: More specifically, the invention includes the use of said compounds for promoting seed germination of a plant species. The present invention also relates to compositions, formulations and germination media comprising said compounds as well as the use of said compositions, formulations and germination media for the treatment of biological plant material including but not restricted to seeds thereof.

BACKGROUND ART

Smoke is unique in facilitating the germination of over 400 native Australian species and a wide range of species from the Mediterranean basin, California, South Africa and Chile (for a review see Brown and Van Staden (1997)). Facilitating the germination of plants is important in a range of fields, including biodiversity conservation, horticulture, agriculture and land restoration. However, existing uses of smoke to facilitate germination require the use of crude or semi-purified smoke. Crude or semi-purified smoke is difficult to handle, potentially toxic at high levels, messy to produce, difficult to reproduce and unable to be produced at sufficient levels to enable cost-effective broad scale use.

Unsurprisingly then, efforts have been made to identify the compound or compounds in smoke responsible for its germination activity. A detailed study by Baldwin et al. (1994) identified 71 compounds in germination promoting fractions of smoke and tested a total of 233 compounds, none of which significantly promoted the germination of *Nicotiana attenuata*. Van Staden et al. (1995) identified 12 compounds through bioassay-guided fractionation of smoke extracts from *Passerina vulgaris* and *Themeda triandra*. They found 7 compounds common to both extracts, 4 of which were available commercially, though found to be inactive. Dixon et al. (1996) identified a suite of compounds through bioassay-guided fractionation of cellulose smoke water and plant-derived smoke water. Testing of available compounds, revealed a further 20 compounds not to be active.

Thus, to this point, it has not been possible to emulate the germination activity of smoke in a convenient or broadly applicable manner.

SUMMARY OF THE INVENTION

This invention resides in a hitherto unknown class of chemical compounds, 2H-furo[2,3-c]pyran-2-ones including derivatives and analogues thereof. It includes methods for making compounds within said class and includes, without limitation, at least the intermediates employed in the generation of said compounds.

More broadly, in one sense, this invention also relates to the use of vinylogous 4H-pyrones, including but not limited to the hitherto unknown 2H-furo[2,3-c]pyran-2-ones.

The utilities to which compounds of the invention may be put will be apparent from reading this specification as a whole. In one aspect the invention resides in a method comprising the step of: exposing biological plant material to at least a compound of the invention to promoting bioactivity within said material.

In another aspect the invention resides in methods for promoting or regulating growth of plant material in, for example, smoke-responsive plant species by exposing said material to a compound of the invention. More specifically, the invention relates to the use of said compounds for promoting seed germination of a plant, for example, a smoke-responsive plant.

The invention also relates to compositions, formulations and germination media comprising said compounds as well as the use of said compositions, formulations and germination media for the treatment of plant species including but not restricted to seeds thereof.

Other objects, features, and advantages of the instant invention, in its details as seen from the above, and from the following description of the preferred embodiment when considered in light of the appended claims.

DETAILED DESCRIPTION OF THE INVENTION

General

Figure 1:
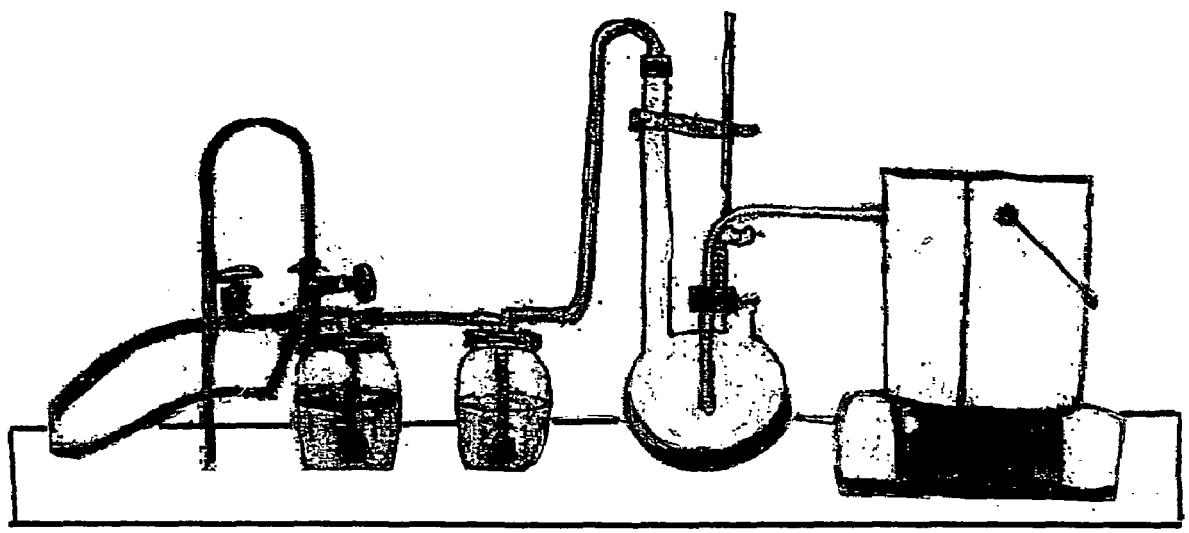
FIG. 1 shows an apparatus used to generate and trap compounds in cellulose-derived smoke.

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used herein the term "derived" and "derived from" shall be taken to indicate that a specific integer may be obtained from a particular source albeit not necessarily directly from that source.

As used herein the terms "bioactivity" or "biological activity" shall be used interchangeably herein and shall be taken to include, without limitation, any type of biological, chemical, biochemical activity initiated, potentiated, retarded or inhibited in plant material by use of compounds of the invention.

As used herein the term "plant material" shall be taken to include, without limitation: any form of vegetative growth including both underground or aboveground for example grasses; plants; vegetables; shrubs; bushes; trees; seeds and seed pods (including nuts etc); roots; tubers; corms; rhizomes; stems; leaves; flowers; fruits; as well as clonally derived material from any of this matter. This includes, horticultural and agricultural species, including in particular all varieties of tobacco, parsley and celery.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within this specification and apply throughout. Unless otherwise defined, all other scientific and technical terms used herein have the same meaning as commonly understood to one of ordinary skill in the art to which the invention belongs.

DESCRIPTION OF PREFERRED EMBODIMENTS

The present invention comprises a compound having the formula (1):

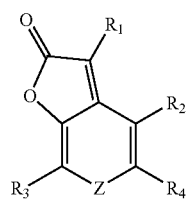

Wherein;
Z is O, S or $NR_5$;
$R_1$, $R_2$, $R_3$, $R_4$ are each independently H, alkyl, alkenyl, alkynyl, phenyl, benzyl, hydroxy, hydroxyalkyl, alkoxy, phenyloxy, benzyloxy, CN, $COR_6$, $COOR_6$, halogen, $NR_6R_7$, or $NO_2$; and
$R_5$, $R_6$, $R_7$ are each independently H, alkyl or alkenyl.

Unless otherwise indicated, alkyl groups having three or more carbon atoms may be straight chain or branched. In addition, alkenyl or alkynyl groups having four or more carbon atoms, or alkoxy groups having more than three carbon atoms may be straight chain or branched. Further, alkyl, alkenyl, alkynyl, alkoxy, phenyl, phenyloxy groups may be optionally substituted with one or more halogens. Further, phenyl, phenyloxy, benzyl, benzyloxy may be optionally substituted with one or more alkyl, alkenyl, alkynyl, hydroxy, alkoxy or hydroxyalkyl groups.

As used herein the term 'halogen' includes fluoro, chloro, bromo or iodo.

Preferably, the present invention comprises a compound having the formula (1):

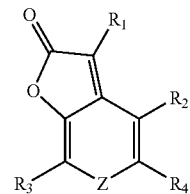

Wherein;
Z is O or $NR_5$;
$R_1$, $R_2$, $R_3$, $R_4$ are each independently H, alkyl, alkenyl, alkynyl, phenyl, benzyl, hydroxy, hydroxyalkyl, alkoxy, phenyloxy, benzyloxy, $COR_6$, $COOR_6$, halogen, $NR_6R_7$, or $NO_2$; and
$R_5$, $R_6$, $R_7$ are each independently H, alkyl or alkenyl.

Preferably still, the present invention comprises a compound having the formula (1):

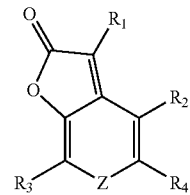

Wherein:
Z is O or $NR_5$;
$R_1$, $R_2$, $R_3$, $R_4$ are each independently H, alkyl, hydroxyalkyl, or alkoxy; and
$R_5$ is H or alkyl.

In an even more preferred form, the present invention comprises a compound having the formula (1'):

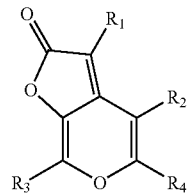

Wherein:
$R_1$, $R_2$, $R_3$, $R_4$ are each independently H, alkyl, hydroxy, hydroxyalkyl, alkoxy, $COR_5$, $COOR_5$ or halogen; and
$R_5$ is H or alkyl.

Preferably still, the present invention comprises a compound having the formula (1'):

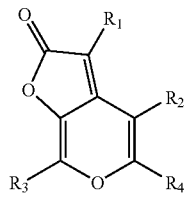

Wherein:

$R_1$, $R_2$, $R_3$, $R_4$ are each independently H or alkyl.

In a highly preferred form of the invention, alkyl and alkoxy groups in either formula 1 or 1' are desirably $C_1$-$C_4$, and alkenyl and alkynyl groups are $C_2$-$C_4$.

In a specific form, the compound of the invention is selected from: 3-methyl-2H-furo[2,3-c]pyran-2-one (where $R_1$=$CH_3$, $R_2$, $R_3$, $R_4$=H), 2H-furo[2,3-c]pyran-2-one (where $R_1$, $R_2$, $R_3$, $R_4$=H), 7-methyl-2H-furo[2,3-c]pyran-2-one (where $R_1$, $R_2$, $R_4$=H, $R_3$=$CH_3$), 5-methyl-2H-furo[2,3-c]pyran-2-one (where $R_1$, $R_2$, $R_3$=H, $R_4$=$CH_3$), 3,7-dimethyl-2H-furo[2,3-c]pyran-2-one (where $R_1$, $R_3$=$CH_3$, $R_2$, $R_4$=H), 3,5-dimethyl-2H-furo[2,3-c]pyran-2-one (where $R_1$, $R_4$=$CH_3$, $R_2$, $R_3$=H), 3,5,7-trimethyl-2H-furo[2,3-c]pyran-2-one (where $R_1$, $R_3$, $R_4$=$CH_3$, $R_2$=H), 5-methoxymethyl-3-methyl-2H-furo[2,3-c]pyran-2-one (where $R_1$=$CH_3$, $R_2$, $R_3$=H, $R_4$=$CH_2OCH_3$), 4-bromo-3,7-dimethyl-2H-furo[2,3-c]pyran-2-one (where $R_1$, $R_3$=$CH_3$, $R_2$=Br, $R_4$=H), 3-methylfuro[2,3-c]pyridin-2(3H)-one (where Z=NH, $R_1$=$CH_3$, $R_2$, $R_3$, $R_4$=H), 3,6-dimethylfuro[2,3-c]pyridin-2(6H)-one (where Z=N—$CH_3$, $R_1$=$CH_3$, $R_2$, $R_3$, $R_4$=H).

The compounds of formula 1 or 1' may contain one or more asymmetric centres and thus may exist as enantiomers or diastereomers. The invention includes both mixtures and separate individual isomers.

The compounds of formula 1 or 1' may also exist in tautomeric forms and the invention includes both mixtures and separate individual tautomers.

Although compounds of the invention may reside in a pure form, the invention is not so limited. Thus, according to the invention there is provided a compound of formula 1 or 1' in an enriched, substantially pure state, substantially homogeneous state, isolated state or a concentrated state.

As used herein the term "enriched" shall describe a state where the relative concentration of a compound of the invention is increased above concentration of the same compound found in smoke.

As used herein the terms "substantially pure" and "substantially homogenous" are used interchangeably to describe a state of separation of the compound of the invention compared to other compounds that ordinarily accompany those compounds in smoke. To this extent a compound of the invention will said to be in such a state of separation when it is separated from one or more of the other compounds that ordinarily accompany the compound of the invention in smoke.

As used herein the terms "isolated or" "concentrated" are used interchangeably to describe a state of separation of a compound of the invention wherein the compound represents 0.00001, 0.0001, 0.001, 0.01, 0.1, 1, 5, 10, 15, 20, 25, 30, 35, 40, 45, 50, 55, 60, 65, 70, 75, 80, 85, 90, 95, 96, 97, 98, 99, 99.5, 99.99 or 100 percent relative wt % of the compound sample. Preferably the compound will represent greater than 1, 5, 10, 15, 20, 25, 30, 35, 40, 45, 50, 55, 60, 65, 70, 75, 80, 85, 90, 95, 96, 97, 98, 99, 99.5, 99.99 or 100 percent relative wt % of the compound sample. In an illustrative manner of assessing such a state, the determination will be made using standard chemical techniques when the compound of the invention is prepared in solid form and before it is combined with other compounds or chemicals with which it may be delivered. The skilled reader should appreciate that such determinations can also be made when the compounds exist in a liquid or gaseous phases and that determination in such forms is not excluded from the invention.

Methods for determining whether a compound of the invention is enriched, substantially pure, substantially homogeneous, isolated, or concentrated will include well known methods of chemical quantification. Those methods will be known to the person skilled in the art. Illustrative examples of such methods include HPLC, GC, GCMS, NMR (including carbon-13 and proton) techniques.

According to a highly preferred embodiment, the invention is an enriched, substantially pure, substantially homogeneous, isolated or concentrated compound selected from: 3-methyl-2H-furo[2,3-c]pyran-2-one, 2H-furo[2,3-c]pyran-2-one, 7-methyl-2H-furo[2,3-c]pyran-2-one, 5-methyl-2H-furo[2,3-c]pyran-2-one, 3,7-dimethyl-2H-furo[2,3-c]pyran-2-one, 3,5-dimethyl-2H-furo[2,3-c]pyran-2-one, 3,5,7-trimethyl-2H-furo[2,3-c]pyran-2-one, 5-methoxymethyl-3-methyl-2H-furo[2,3-c]pyran-2-one, 4-bromo-3,7-dimethyl-2H-furo[2,3-c]pyran-2-one, 3-methylfuro[2,3-c]pyridin-2(3H)-one, 3,6-dimethylfuro[2,3-c]pyridin-2(6H)-one or a biologically active analogue thereof.

The invention also includes radio-labelled derivatives of the compounds of formula 1 or 1', which are suitable for biological studies. Such radio labels include for example isotopes such as: $^3H$, $^{14}C$, $^{32}P$, $^{35}S$, $^{125}I$ or $^{131}I$. The radioactive isotope can be detected by such means as the use of a gamma counter or a scintillation counter or by autoradiography.

In a second embodiment, the invention provides a method for the preparation of a compound of formula 1 or 1', the method comprising the step of: treating a compound having the formula (2):

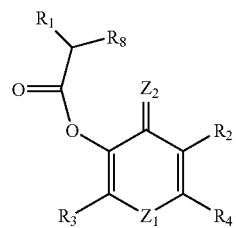

wherein:

$Z_1$ is O, S, or $NR_5$;

$Z_2$ is O or S;

$R_8$ is H, Cl, Br, or $PO(OEt)_2$ $R_1$, $R_2$, $R_3$, $R_4$ are each independently H, alkyl, alkenyl, alkynyl, phenyl, benzyl, hydroxy, hydroxyalkyl, alkoxy, phenyloxy, benzyloxy, CN, $COR_6$, $COOR_6$, halogen, $NR_6R_7$ or $NO_2$; and $R_5$, $R_6$, $R_7$ are each independently H or alkyl.

with acetic anhydride or propionic anhydride.

Preferably, the present invention comprises the step of: treating a compound having the formula (2):

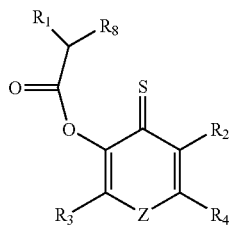

2 wherein:
Z is O or NR$_5$;
R$_1$, R$_2$, R$_3$, R$_4$ are each independently H, alkyl, alkenyl, alkynyl, phenyl, benzyl, hydroxy, hydroxyalkyl, alkoxy, phenyloxy, benzyloxy, COR$_6$, COOR$_6$, halogen, NR$_6$R$_7$ or NO$_2$;
R$_5$, R$_6$, R$_7$ are each independently H or alkyl; and
R$_8$ is Cl or Br.

with acetic anhydride or propionic anhydride.

Alternately, there is provided a method for the preparation of a compound of formula 1 or 1', the method comprising the step of heating a compound of formula (2) under reflux using a suitable solvent. Illustrative solvents that are suitable for such purposes include acetic anhydride, propionic anhydride, acetone, acetonitrile, tetrahydrofuran, dioxane, dichloromethane, chloroform, ether, pyridine, anisole, dimethyl formamide, dimethyl sulfoxide, benzene, toluene and ethyl acetate.

Alternately, there is provided a method for the preparation of a compound of formula 1' or 1', the method comprising the step of: treating a compound of formula (2) with a base in a suitable solvent. Illustrative bases that are suitable for such purposes include: 1,8-Diazabicyclo[5.4.0]-undec-7-ene (DBU), lithium di-isopropyl amide (LDA), lithium hexamethyl disilazide (LiHMDS), triethylamine, pyridine, potassium t-butoxide, sodium hydride, sodium methoxide, sodium ethoxide, sodium acetate, sodium or potassium carbonate, sodium or potassium hydroxide.

Alternately, there is provided a method for the preparation of a compound of formula 1 or 1', the method comprising the step of: treating a compound of formula (2) with a base and a thienophile (desulfurizing agent) in a suitable solvent. Illustrative thienophiles that are suitable for such purposes include: triphenyl phosphine, tributyl phosphine, triethyl phosphine, trimethyl phosphine, tributyl phosphite, triethyl phosphite and trimethyl phosphite.

In a further alternative, there is provided a method for the preparation of a compound of formula 1 or 1', the method comprising the steps of heating a compound of formula (2) under reflux using a suitable solvent followed by treatment with a base in a suitable solvent in the presence or absence of a desulfurising agent. Illustrative bases, solvents and thienophiles that may be used for this step in the method will include those bases, solvents and desulfurising agents listed in the preceding paragraphs.

The following provides a single non-limiting illustration of how the compounds of formula 1 or 1' may be generated. A mixture of anhydrous sodium acetate and triphenyl phosphine in acetic anhydride is heated. A solution of the thione 2-haloester illustrated as formula 2 is diluted in acetic anhydride and added drop wise to the heated mixture. The mixture is heated for a suitable amount of time and allowed to cool. The dark mixture is poured into a liquid such as ice/water and stirred until one phase is formed. The aqueous solution is filtered and extracted with a solvent such as dichloromethane. The organic extract is washed, dried, filtered and evaporated to dryness. The crude residue can then be directly chromatographed to produce the compounds of formula 1 or 1'. Alternatively, the crude residue can be extracted with potassium carbonate solution with gentle heating. The resultant solution is filtered and extracted. The organic extract is washed, dried, filtered and evaporated to dryness to give a residue, which is chromatographed to produce the compounds of formula 1 or 1'

Where the compound of the invention is 3-methyl-2H-furo[2,3-c]pyran-2-one, the compound of formula (2) is 4-thioxo-4H-pyran-3-yl 2-chloropropanoate.

In a more specific method for the preparation of a compound of formula 1 or 1', the method for the preparation of a compound of formula (1) further comprises the step of: producing the compound of formula (2) by the step of treatment of a compound having the formula (3):

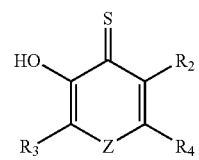

3 wherein;
Z$_1$ is O, S or NR$_5$;
Z$_2$ is O or S;
R$_2$, R$_3$, R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$ or NO$_2$; and
R$_5$, R$_6$, R$_7$ are each independently H or alkyl.

with a compound having the formula (3a):

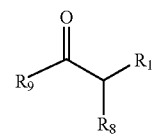

3a wherein:
R$_1$ is H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$ or NO$_2$;
R$_6$, R$_7$ are each independently H or alkyl;
R$_8$ is H, Cl, Br, or PO(OEt)$_2$; and
R$_9$ is Cl or Br.

In a modified and more preferable form of the above step in the method, the present invention comprises the step of producing the compound of formula (2) by the step of treatment of a compound having the formula (3'):

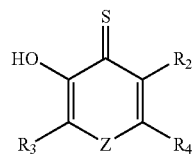

3' wherein;
Z is O or NR$_5$;
R$_2$, R$_3$, R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$ or NO$_2$; and R$_5$, R$_6$, R$_7$ are each independently H or alkyl with a compound having the formula (3a'):

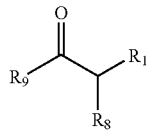

3a' wherein;
R$_1$ is H, alkyl, alkenyl, alkynyl, phenyl, benzyl, hydroxy, hydroxyalkyl, alkoxy, phenyloxy, benzyloxy, COR$_6$, COOR$_6$, halogen, NR$_6$R$_7$ or NO$_2$;
R$_6$, R$_7$ are each independently H or alkyl;
R$_8$ is H, Cl or Br; and
R$_9$ is Cl or Br.

Where the compound of formula (2) is 4-thioxo-4H-pyran-3-yl 2-chloropropanoate, the compound of formula (3) is 3-hydroxy-4H-pyran-4-thione and is treated with 2-chloropropionyl chloride.

The following provides a single non-limiting illustration of how the compounds of formula 2 may be generated. Compound 3a or 3a' is added to a solution of the thione alcohol as depicted by formula 3 or 3' and triethylamine in dry dichloromethane and the solution is stirred for a suitable amount of time. The mixture is evaporated to dryness and the residue is purified to give a compound of formula 2.

Where the compound of formula (2) is 4-thioxo-4H-pyran-3-yl 2-chloropropanoate, the compound of formula 3 or 3' is 3-hydroxy-4H-pyran-4-thione and is treated with 2-chloropropionyl chloride.

In a more specific method for the preparation of a compound of formula 1 or 1', the method for the preparation of a compound of formula (1) further comprises the step of: producing a compound of formula (3) by the step of treatment of a compound of formula (4):

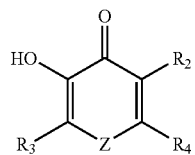

4 wherein;
Z is O, S or NR$_5$;
R$_2$, R$_3$, R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$, NO$_2$; and
R$_5$, R$_6$, R$_7$ are each independently H or alkyl with phosphorous pentasulphide.

In a modified and more preferably form of the above step in the method, the present invention comprises the step of: producing a compound of formula (3) by the step of treatment of a compound of formula (4'):

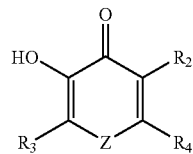

4' wherein;
Z is O or NR$_5$;
R$_2$, R$_3$, R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$, NO$_2$; and
R$_5$, R$_6$, R$_7$ are each independently H or alkyl with phosphorous pentasulphide.

The following provides a single non-limiting illustration of how the compounds of formula 2 may be generated. Following the general method of Scheeren et al. (1973) which is incorporated herein by reference, phosphorus pentasulphide in tetrahydrofuran is added to a stirred solution of the carbonyl compound disclosed in formula 4 or 4' and dissolved in tetrahydrofuran. Solid sodium hydrogen carbonate is added and the reaction mixture stirred at room temperature for a suitable amount of time. The reaction mixture is poured into water and extracted with ethyl acetate. The combined organic extract is washed with brine, dried, filtered and evaporated to dryness. The crude residue is purified to yield compounds of formula 3 or 3'.

Where the compound of formula (3) is 3-hydroxy-4H-pyran-4-thione, the compound of formula (4) is 3-hydroxy-4H-pyran-4-one (pyromeconic acid).

In addition to providing methods for the generation of the compounds described herein it will be understood that the invention includes the compounds so produced by said methods. Thus in yet a further aspect the invention comprises a compound of formula 1 or 1' produced by any one or more of the aforementioned methods.

In a third embodiment, the invention also extends to a method for the treatment of plant material, the method comprising the steps of exposing plant material to a biologically active amount of a compound of formula (5):

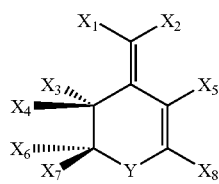

5

Wherein:
Y is O, S, or NX$_9$;
X$_1$, X$_2$ are each independently H, alkyl, alkenyl, alkynyl, phenyl, benzyl, hydroxy, hydroxyalkyl, alkoxy, phenyloxy, benzyloxy, COX$_7$, COOX$_7$, halogen, CN, NX$_{10}$X$_{11}$, NO$_2$, C$_3$ to C$_5$ cycloalkyl, or together with X$_3$, X$_4$ or X$_5$ as a carbolactone;
X$_3$, X$_4$, X$_5$, X$_6$, X$_7$, X$_8$ are each independently H, alkyl, alkenyl, alkynyl, phenyl, benzyl, hydroxy, hydroxyalkyl, alkoxy, phenyloxy, benzyloxy, CN, COX$_{10}$, $COOX_{10}$, halogen, $NX_{10}X_{11}$, $NO_2$ or $X_3$ (or $X_4$) together with $X_6$ (or $X_7$) on $sp^2$-hybridised carbon atoms; and $X_9$, $X_{10}$ and $X_{11}$, are each independently H, alkyl or alkenyl.

or biologically acceptable salts thereof.

Preferably, the compound employed in the method of treatment of a plant material is a compound selected from the formula (5):

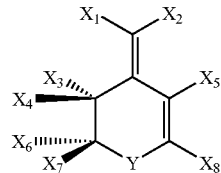

Wherein:

Y is O or $NX_9$;

$X_1$, $X_2$ are each independently H, alkyl, alkenyl, alkynyl, phenyl, benzyl, hydroxy, hydroxyalkyl, alkoxy, phenyloxy, benzyloxy, $COX_7$, $COOX_7$, halogen, $NX_{10}X_{11}$, $NO_2$, $C_3$ to $C_5$ cycloalkyl, or together with $X_3$, $X_4$ or $X_5$ as a carbolactone;

$X_3$, $X_4$, $X_5$, $X_6$, $X_7$, $X_8$ are each independently H, alkyl, alkenyl, alkynyl, phenyl, benzyl, hydroxy, hydroxyalkyl, alkoxy, phenyloxy, benzyloxy, CN, $COX_{10}$, $COOX_{10}$, halogen, $NX_{10}X_{11}$, $NO_2$ or $X_3$ (or $X_4$) together with $X_6$ (or $X_7$) on $sp^2$-hybridised carbon atoms; and $X_9$, $X_{10}$ and $X_{11}$ are each independently H, alkyl or alkenyl.

and biologically acceptable salts thereof.

Even more preferably, the compound employed in the method of treatment of plant material is a compound selected from formula (5'):

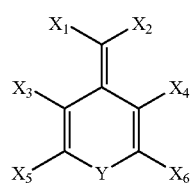

Wherein;

Y is O or $NX_7$;

$X_1$, $X_2$ are each independently H, alkyl, hydroxy, hydroxyalkyl, alkoxy, $COX_8$, $COOX_8$, $NX_8X_9$, $NO_2$, $C_3$ to $C_5$ cycloalkyl, or together with $X_3$ or $X_4$ as a carbolactone;

$X_3$, $X_4$, $X_5$, $X_6$ are each independently H, alkyl, phenyl, benzyl, hydroxy, hydroxyalkyl, alkoxy, phenyloxy, benzyloxy, $COX_8$, $COOX_8$, $NX_8X_9$; and $X_7$, $X_8$ and $X_9$ are each independently H or alkyl.

In a highly desirable form of the invention the compound employed in the method of treatment of plant material is a compound selected from formula (5"):

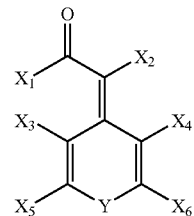

Wherein;

Y is O or $NX_7$;

$X_1$ is H, alkyl, hydroxy, hydroxyalkyl, alkoxy, $C_3$ to $C_5$ cycloalkyl, or together with $X_3$ as a carbolactone;

$X_2$, $X_3$, $X_4$, $X_5$, $X_6$ are each independently H, alkyl, phenyl, benzyl, hydroxy, hydroxyalkyl, alkoxy, phenyloxy, benzyloxy, $COX_8$, $COOX_8$; and $X_7$ and $X_8$ are each independently H or alkyl.

The compounds of formulas 5, 5' or 5" may contain one or more asymmetric centres and thus may exist as enantiomers or diastereomers. The invention includes both mixtures and separate individual isomers.

The compounds of formulas 5, 5' or 5" may also exist in tautomeric forms and the invention includes both mixtures and separate individual tautomers.

The biologically acceptable salts of the compounds of formulas 5, 5' or 5" that contain a basic centre are acid addition salts formed with biologically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Compounds of formulas 5, 5' or 5" may also provide biologically acceptable metal salts, in particular alkali metal salts, with bases. Examples include the sodium and potassium salts.

Without wishing to be bound by theory, it is believed that the compounds of formulas 5, 5' or 5" binds to a receptor by interaction of a nucleophilic group attacking the conjugated diene system. Accordingly, compounds possessing two such conjugated systems are preferred. For example, using a 3-methyl-2H-furo[2,3-c]pyran-2-one (i.e. a specific compound of formula (5)) as an example, the pyran ring provides two points of attack for a nucleophilic group, as illustrated below in Pathways 1 and 2:

PATHWAY 1

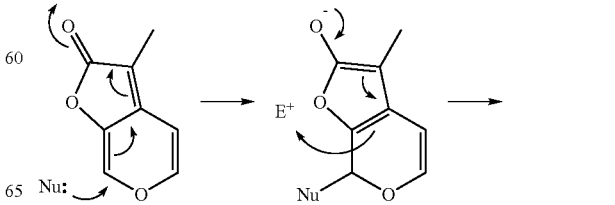

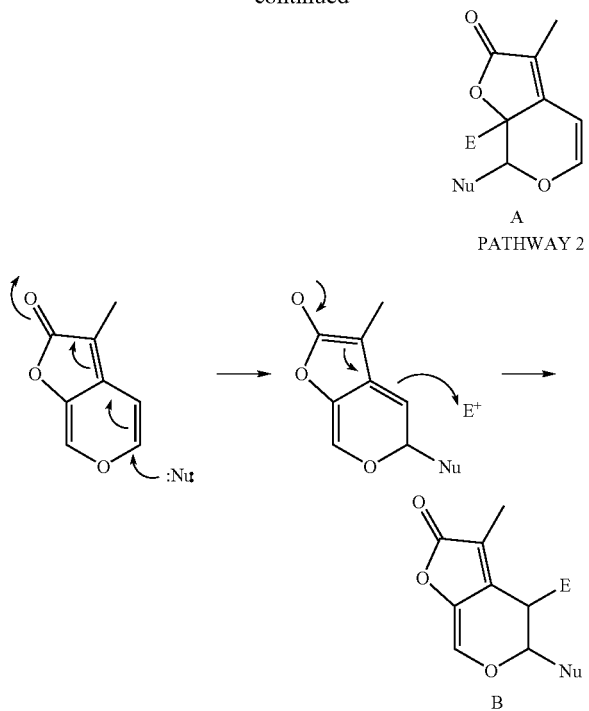

PATHWAY 2

Interestingly, both A and B are primed to accept another nucleophilic group.

Syntheses of certain compounds of formula (5) are described in Belsky et al. (1974) and Ohkata et al. (1986). This teaching is explicitly incorporated herein by reference. Based on this teaching those of ordinary skill in the art will be capable of synthesising other compounds within formula (5).

While this form of the invention describes the invention in terms of the compounds of formulas 5, 5' or 5", in a more preferred form of the invention the method is performed using the compounds of formula 1 or 1'. Even more preferably, the invention is performed using one or more of the specific compounds described herein including biologically active intermediate compounds. In a specific form of the invention, the compound of formula (5) is selected from: 3-methyl-2H-furo[2,3-c]pyran-2-one, 2H-furo[2,3-c]pyran-2-one, 7-methyl-2H-furo[2,3-c]pyran-2-one, 5-methyl-2H-furo[2,3-c]pyran-2-one, 3,7-dimethyl-2H-furo[2,3-c]pyran-2-one, 3,5-dimethyl-2H-furo[2,3-c]pyran-2-one, 3,5,7-trimethyl-2H-furo[2,3-c]pyran-2-one, 5-methoxymethyl-3-methyl-2H-furo[2,3-c]pyran-2-one, 4-bromo-3,7-dimethyl-2H-furo[2,3-c]pyran-2-one, 3-methylfuro[2,3-c]pyridin-2(3H)-one, 3,6-dimethylfuro[2,3-c]pyridin-2(6H)-one, ethyl 2-(4H-pyran-4-ylidene) acetate, ethyl 2-(acetylthio)-2-(4H-pyran-4-ylidene) acetate, 2-(2,6-dimethyl-4H-pyran-4-ylidene)-1-phenylethanone and 2-(2,6-dimethyl-4H-pyran-4-ylidene)-1-phenylethanone.

In accordance with this embodiment of the invention the compounds disclosed herein will have utility in a wide range of plant growth regulating applications. Those applications will generally depend on the germination of plants, but are not limited to such modes of action. Plant growth regulating applications will include, for example, generation of plants, shrubs, grasses and vegetables, weed germination enhancement, grass field germination, amenity and cut flower germination, rangeland germination, natural areas restoration, mine site restoration agricultural and horticultural purposes. The compounds of the present invention may also have application as replacements for other germination stimulating agents including, but not limited to sunlight.

In accordance with this embodiment of the invention the method for the treatment of plant material will comprise the step of: treating a plant material to modify the germination, germination rate, growth or development of said plant material. As used herein 'germination, germination rate, growth or development' includes, without limitation, modification of germination, flowering, fruiting, release from floral or vegetative dormancy and propagation through both in vitro and ex vitro techniques such as somatic embryogenesis.

In another form of this embodiment of the invention there is provided a method for promoting growth of plant material in plant species by exposing said material to a compound of formulas 5, 5' or 5". More preferably, the method is performed using the compounds of formula 1 or 1'. Even more preferably, the invention is performed using one or more of the specific compounds described herein including biologically active intermediate compounds. In a specific form of the invention, the compound of formulas 5, 5' or 5" is selected from 3-methyl-2H-furo[2,3-c]pyran-2-one, 2H-furo[2,3-c]pyran-2-one, 7-methyl-2H-furo[2,3-c]pyran-2-one, 5-methyl-2H-furo[2,3-c]pyran-2-one, 3,7-dimethyl-2H-furo[2,3-c]pyran-2-one, 3,5-dimethyl-2H-furo[2,3-c]pyran-2-one, 3,5,7-trimethyl-2H-furo[2,3-c]pyran-2-one, 5-methoxymethyl-3-methyl-2H-furo[2,3-c]pyran-2-one, 4-bromo-3,7-dimethyl-2H-furo[2,3-c]pyran-2-one, 3-methylfuro[2,3-c]pyridin-2(3H)-one, 3,6-dimethylfuro[2,3-c]pyridin-2(6H)-one, ethyl 2-(4H-pyran-4-ylidene) acetate, ethyl 2-(acetylthio)-2-(4H-pyran-4-ylidene) acetate, 2-(2,6-dimethyl-4H-pyran-4-ylidene)-1-phenylethanone and 2-(2,6-dimethyl-4H-pyran-4-ylidene)-1-phenylethanone.

More specifically, the invention provides a method for facilitating the germination of a seed, said method comprising the step of: exposing said seed to a compound of formulas 5, 5' or 5. The method of the present invention acts to promote seed germination in a broad range of phylogenetically diverse plant groups including species from fire, non-fire, agricultural and horticultural habitats. Even more specifically the method is performed using the compounds of formula 1 or 1'.

Desirably the invention is performed using one or more of the specific compounds described herein including biologically active intermediate compounds. In a specific form of the invention, the compound of formulas 5, 5' or 5" is selected from ethyl 2-(4H-pyran-4-ylidene) acetate, ethyl 2-(acetylthio)-2-(4H-pyran-4-ylidene) acetate, 2-(2,6-dimethyl-4H-pyran-4-ylidene)-1-phenylethanone and 2-(2,6-dimethyl-4H-pyran-4-ylidene)-1-phenylethanone.

In one form of this embodiment of the invention, the plant species is a smoke responsive plant species. Methods for ascertaining whether a plant material is from a smoke responsive plant are described in Dixon et al. (1995), which is herein explicitly incorporated by reference.

While the methods described herein refer to the application of a single compound in the treatment of biological material it will be understood that the scope of the invention will also include combinations of two or more of the compounds described herein.

Methods of the present invention may be employed to regulate the plant development of a wide range of plants. The following list of plants is provided only as an illustration of some of the plants where the invention will have application. Those skilled in the art will know how to test the biological efficacy of the compounds of the invention. Methods such as those described below may be used for this purpose.

Such plants include, without limitation: *Gompholobium tomentosum, Melaleuca carrii, Allium ampeloprasum* (leek), *Petroselinium crispum* (parsley); Weeds such as *Avena fatua* (wild oats), *Brassica toumefortii* (wild turnip), *Acetosa vesicaria* (ruby dock); Amenity horticulture plants such as *Passerina vulgaris, Rhodocoma arida, Syncarpha vestita*; grasses such as *Microlaena stipoides*; Other plant varieties such as—*Borya sphaerocephala, Centrolepis aristate, Cherianthera preissiana, Opercularia vaginate, Emmenanthe penduliflora, Podolepis canescens, Echinacea angustiflora, Baloskion tetraphyllum.*

Smoke responsive plant species have been found to be particularly responsive to the methods of the invention. Known smoke responsive genera and species native to Australia include but may not be limited to *Acacia, Acanthocarpus, Acrotriche, Actinostrobus, Actinotus, Actinostrobus acuminatus, Adenanthos barbigerus, Agonis, Agrostocrinum scabrum, Allocasuarina fraseriana, Alyogyne hakeifolia, Alyogyne huegelii, Alyxia, Amphipogon amphopogonoides, Andersonia, Angallis arvensis, Anigozanthos manglesii, Anigozanthos bicolor, Anigozanthos humilis, Anigozanthos rufus, Arthropodium, Astartea, Astroloma, Audonia capitata, Baeckea, Banksia collina, Banksia cuneata, Banksia grandis, Banksia paludosa, Banksia marginata, Baumia articulata, Billardiera bicolor, Billardiera coeruleo-punctata, Billardiera varifolia, Billardiera scandens, Blancoa, Boronia fastigata, Boronia tenuis, Bossiaea aquifolium, Bossiaea ornata, Bossiaea viscosa, Brunonia, Brachyloma preissii, Burchardia umbellata, Bursaria, Caesia, Callitris, Calytrix breviseta, Calytrix depressa, Calytrix fraserii, Calytrix tetragona, Chamaescilla corymbosa, Chieranthera, Chloris ventricosa, Clematis pubescens, Chionochloa pallida, Codonocarpus, Comesperma virgatum, Conospermum incurvcum, Conospermum triplinervium, Conostephium, Conostylis aculeata, Conostylis candicans, Conostylis neocymosa, Conostylis setosa, Conostylis serrulata, Conyza albida, Crassula, Croninia kingiana, Cryptandra, Cyathochaeta avenacea, Dampiera, Desmocladus, Dianella, Dichanthium sericeum, Digitaria diffusa, Digitaria ramularis, Diplolaena, Drosera, Echinacea purpurea, Entolasia stricta, Epacris, Eragrostis brownii, Eremophila longifolia, Eriostemon spicatus, Escholzia californica, Eucalyptus calophylla, Eucalpytus marginata, Eucalpytus obliqua, Eucalyptus pauciflora, Eucalpytus radiata, Exocarpus, Gahnia, Exocarpus sparteus, Geleznowia verrucosa, Georgiella, Glischrocaryon aureum, Gompholobium marginatrum, Gompholobium preissii, Gonocarpus, Grevillea polybotrya, Grevillea quercifolia, Grevillea stenobotrya, Grevillea wilsonii, Gyrostemon ramulosus, Haemodorum, Hakea amplexicaulis, Hakea corymbosa, Hakea cyclocarpa, Hakea lissocarpha, Hakea ruscifolia, Hakea stenocarpa, Hakea undulata, Hemiandra pungens, Hemigenia ramosissima, Hemiphora, Heteropogon contortus, Hibbertia amplexicaulis, Hibbertia lasiopus, Hibbertia quadricolor, Hibbertia riparia, Hibbertia sericea, Hovea chorizemifolia, Hovea trisperma, Hyalosperma cotula, Hybanthus, Hydrocotyle callicarpa, Hypericum gramineum, Hypocalymma angustifolium, Hypocalymma robustum, Isopogon, Isotoma hypocrateriformis, Johnsonia, Joycea pallida, Kennedia coccinea, Kennedia prostrate, Lachnostachys, Lagenifera huegelii, Lasiopetalum, Lawrencella davenportii, Laxmannia, Lechenaultia biloba, Lechenaultia floribunda, Lechenaultia formosa, Lechenaultia macrantha, Lepidosperma longitudinale, Leptomeria, Leptospermum, Leucanthemum x superbum, Leucopogon, Levenhookia pusilla, Lomandra longifolia, Lomandra multiflora, Loxocarya, Lysinema ciliatum, Macropidia, Melaleuca, Mirabelia dilatata, Mitrasacme, Myriocephalus, Neurachne alopecuroidea, Opercularia brownii, Opercularia diphylla, Opercularia echinocephala, Orthrosanthus laxus, Panicum decompositum, Paronychia, Paspalidium gausam, Patersonia fragilis, Patersonia occidentalis, Persoonia longifolia, Petrophile drummondii, Petrophile linearis, Philotheca, Phyllanthus calycinus, Pimelea ciliata, Pimelea imbricate, Pimelea spectabilis, Pimelea suaveolens, Pimelea sulphurea, Pimelea sylvestris, Pityrodia, Platysace compressa, Platysace tenuissima, Poa labillardieri, Pomaderris, Poranthera microphylla, Protea, Ptilotus, Restio sinuosus, Ricinocarpus, Rulingia platycalyx, Scaevola calliptera, Scaevola crassifolia, Siegfriedia darwinoides, Siegfriedia globulosus, Sisyrinchium, Sollya heterophylla, Sowerbaea, Sphenotoma capitatu, Spyridium, Stackhousia pubescens, Stipa compressa, Stirlingia latifolia, Stylidium amoenum, Stylidium affine, Stylidium brunoniamum, Stylidium bulbiferum, Stylidium calcaratum, Stylidium hispidum, Stylidium junceum, Stylidium schoenoides, Tersonia, Tetraria, Tetrarrhena laevis, Tetratheca hirsuta, Themeda triandra, Thomasia angustifolia, Thysanotus fastigiatus, Thysanotus multiflorus, Trachymene pilosa, Trichocline, Triodia longiceps, Tripterococcus brunonis, Trymalium ledifolium, Velleia, Verticordia aurea, Verticordia chrysantha, Verticordia densiflora, Verticordia eriocephala, Verticordia huegelii, Wahlenbergia gracilis, Waitzia, Xanthorrhoea, Xanthosia candida, Xanthosia heugelii; Askindiosperma andreanum, Audouinia capitata, Aulax cancellatat, Berzelia lanuginose, Cannomois virgatat, Chondropetalum, Cyclopia intermedia, Dovea macrocarpa, Edmondia sesamoides, Elegia, Erica, Helichrysum, Ischyrolepis, Leucospermum, Lobelia, Metalasia densa, Pahenocoma prolifera, Pelargonium, Protea, Restio, Senecio, Serruria, Staberoha, Syncarpha, Thamnochortus, Themeda triandra, Widdringtonia cuppressioides, Cistus cripus, Cistus ladanifer, Cistus monspeliensis, Cistus salviifolius, Dactylis glomerate, Dittrichia viscose, Retama sphaerocarpa, Senecio jacobaea, Trifolium angustifolium, Allophyllum glutinosum, Antirrhinum coulterianum, Antirrhinum kelloggii, Antirrhinum nuttallianum, Antirrhinum multiflorum, Antirrhinum terianum, Camissonia californica, Chaenactis artemislifolia, Cryptantha clevelandi, Cryptantha micrantha, Caulanthus heterophyllus, Emmenanthe penduliflora, Eriodictyon, Eschscholzia californica* (Californian Poppy), *Eucrypta chrysanthemifolia, Nicotiana attenuata, Mentzelia micrantha, Mimulus brevipes, Mimulus clevelandii, Penstemon centranthifolius, Penstemon sprectabilis, Penstemon centranthifolius, Phacelia grandiflora, Phacelia minor, Romneya coulteri, Salvia apiana, Salvia columbariae, Salvia leucophylla, Salvia mellifera, Silene multinervia, Turricula, Echinacea purpurea, Echinacea purpurea* (Bravado), *Dionaea* (Venus' Flytrap), and *Calluna vulgaris*. Other known smoke responsive species include 'Grand Rapids' Lettuce Seed, Sweet Basil.

Compounds of formula 5, 5' or 5" are likely to be bioactive with all future species shown to be responsive to various applications of smoke.

In a highly specific form of the invention, the plant material is a seed of a species selected from the following group: 'Grand Rapids' Lettuce Seed, *Stylidium affine, Conostylis aculeata, Brunonia australis, Conostylis candicans, Grevillea polybotrya, Lawrencella davenportii, Ozothamnus cordifolium, Scaevola thesioides, Verticordia densiflora, Passerina vulgaris, Rhodocoma arida, Syncarpha vestita, Camissonia californica, Caulanthus heterophyllus, Emmenanthe penduliflora,* and *Nicotiana attenuata.*

According to the methods of treatment described herein, the compound of formula 5, 5' or 5" may be exposed to the plant material by any of a variety of methods.

For example, the compounds can be applied directly or as a composition in the form of a liquid or solid to the plant material, to seeds or to other media in which the plant material is grown or growing or to be planted, or they can be sprayed on, dusted on or applied as a cream or paste formulation, or they can be applied as a vapour. The compounds can also be applied directly or as a composition to soil surrounding the roots of plant material, for systemic activity, or to a seed before it is planted. If used for hydroponic culture, direct addition to the nutrient solution may be possible. The timing of the application is not particularly critical, and the formulations can be applied at seeding or at transplanting time.

In one form the compounds of the invention can be applied in the form of liquid preparations for use as liquids, dips or sprays which are generally aqueous dispersions or emulsions. For preparation of the liquid formulation, selection of any additional surfactants in the liquid form is important. The surfactant should possess the following properties: it must be capable of dissolving the compound of formula 5 or 5' or 5" or more specifically formula 1 or 1'; it must not affect the stability of the active ingredient; it will preferably mix well with water; it must have a low phytotoxicity; and it must have a relatively high boiling point. The liquid formulation can be prepared by dissolving the compound of formula 5 or 5' or 5" or more specifically formula 1 or 1' in one or more of the surfactants mentioned below or in a mixture of one or more of these surfactants with water.

Surfactants suitable for use in this form of the invention include, for example, wetting agents, dispersing agents, emulsifying agents or suspending agents. These agents can be cationic, anionic or non-ionic agents such as:

(1) Suitable cationic agents are the higher aliphatic amines and ethylene oxide condensates with such amines; quaternary ammonium salts, e.g. chlorides and cetyltrimethylammonium bromide; N-alkylamine acetates; and N-alkylamine oxides;

(2) Suitable anionic agents are aryl sulfonate salts, especially alkylbenzenesulfonates and alkylnaphthalenesulfonate, such as sodium isopropylnaphthalenesulfonate, sodium methylenebisnaphthalenesulfonate, and sodium dodecylbenzenesulfonate; phosphates or sulfates of polyoxyethylenealkyl or alkylallyl ethers; .beta.-naphthalenesulfonate-formalin condensate salts; ligninsulfonates, such as sodium ligninsulfonate; polymer surfactants of the polycarboxylate and/or polysulfonate type; condensed phosphates, such as sodium hexametaphosphate or sodium tripolyphosphate; salts of higher fatty acids, i.e. soaps, e.g. sodium oleate; salts, e.g. sodium and calcium salts, of sulfonic acids and the acids themselves, e.g. ligninsulfonic acid, and or alkyl sulfonate salts, especially sodium dialkyl sulfosuccinates, such as sodium dioctyl sulfosuccinate or sodium 2-ethylhexenesulfonate and equivalent salts with metals other than sodium; salts, e.g. sodium, ammonium and amine salts, of polyoxyethylene alkyl aryl ether sulfates or of polyoxyethylene alkyl ether sulfates or the free acids; or salts of polyoxyethylene alkyl aryl ether phosphates or of polyoxyethylene alkyl phosphates; and alkyl sulfate salts, such as sodium lauryl sulfate or oleyl sulfate amine salt; and (3) Suitable non-ionic agents are the condensation products of ethylene oxide with fatty alcohols such as oleyl or cetyl alcohol, or with alkyl phenols such as octyl- or nonylphenol and octylcresol. Other non-ionic agents are polyoxyethylene alkyl ethers, polyoxyethylene alkylallyl ethers, oxyethylene/oxypropylene block polymers, the polymerization adducts of ethylene oxide with higher alcohols, such as lauryl alcohol, stearyl alcohol and oleyl alcohol; the polymerization adducts of ethylene oxide with alkylphenols, such as isooctylphenol or nonylphenol; the polymerization adducts of ethylene oxide with alkylnaphthols, such as butyinaphthol or octyinaphthol; the polymerization adducts of ethylene oxide with higher fatty acids, such as palmitic acid, stearic acid or oleic acid; the polymerization adducts of ethylene oxide with mono- or di-alkylphosphoric acids, such as stearylphosphoric acid or dilaurylphosphoric acid; the polymerization adducts of ethylene oxide with amines, such as dodecylamine; amides or ethoxylated amides of higher fatty acids, such as stearamide; higher fatty acid esters of polyhydric alcohols, such as sorbitan, and the polymerization adducts of ethylene oxide therewith; higher fatty acid esters of glycerol borates or of ethoxylated glycerol borates; and glycerides and sucrose esters of fatty acids.

The compounds of the invention for use as aqueous dispersions or emulsions are generally supplied in the form of a concentrate containing a high proportion of the active ingredient. The concentrates are then diluted with water before use. These concentrates often should be able to withstand storage for prolonged periods and after such storage be capable of dilution with water in order to form aqueous preparations which remain homogeneous for a sufficient time to enable them to be applied by conventional equipment.

For those compounds of formula 5, 5' or 5" that are aqueous in water, the plant material is conveniently exposed to an aqueous solution of the compound of formula 5, 5' or 5". The aqueous solution of the compound of formula 5, 5' or 5" preferably comprises between about 10 mg/L to about $1 \times 10^{-4}$ mg/L of the compound of formula 5, 5' or 5".

To prepare emulsions, pastes or oil dispersions, the derivatives, as such or dissolved in a solvent, can be homogenized in water by means of wetting agent, tackifier, dispersant or emulsifier. Alternatively, it is possible to prepare concentrates composed of active substance, wetting agent, tackifier, dispersant or emulsifier and, if appropriate, solvent or oil, and these concentrates are suitable for dilution with water.

The compounds of the invention may be used as sprays in the form of aerosols wherein the formulation is held in a container under pressure in the presence of a propellant, such as, for example, fluorotrichloromethane or dichlorodifluoromethane.

The compositions may be in the form of powders or granules comprising the active ingredient and a solid diluent or carrier.

Powders, materials for scattering and dusts can be prepared by mixing or grinding the active substances together with a solid carrier. Alternatively a powder formulation can be obtained by mixing compounds of formula 1 or 1' or formula 5 or 5' or 5" with a fine powder of a mineral substance, for example, clay, talc or calcium carbonate after which the mixture is pulverized, preferably using a pulverizer of the swing-hammer type.

A powder coating formulation can be obtained by mixing the compounds of formula 1 or 1' or formula 5 or 5' or 5" with any other conventional additives, optionally after adding a filler. Examples of fillers which may be employed are disclosed above. Additives which may be used for the preparation of dust coating formulations include surfactants, such as the non-ionic surfactant and anionic surfactants exemplified above; binders and thermoplastic resin powders. Examples of binders which may be employed for maintaining and binding the active ingredients onto the surfaces of seeds, include water-soluble high molecular weight compounds, for example, water-soluble polysaccharides, such as alginic acid and salts thereof, carboxymethylcellulose and salts thereof, methylcellulose, polyvinyl alcohol, sodium polyacrylate, polyethylene oxide, polyvinylpyrrolidone or xanthan gum. Examples of thermoplastic resin powders having a membrane-forming capacity which may be employed include ethylene-vinyl chloride copolymer resin powder, ethylene-vinyl acetate copolymer resin powder and vinyl chloride resin powder. The powder coating formulation may be prepared by combining the active ingredient with one or more of these additives, depending on the purpose of the formulation. Granules, for example coated granules, impregnated granules and homogeneous granules, can be prepared by binding the active ingredients to solid carriers. Solid carriers are mineral earths such as silicas, silica gels, silicates, solid carrier materials that may be used include lime, kaolin, chalk, talc, attaclay and other clays as well as inorganic substances, such as clays (examples of which are bentonite, kaolinite, montmorillonite and attapulgite), dolomite, talc, mica, aggalmatolite, pyrophyllite, pumice, vermiculite, gypsum, bole, loess, diatomaceous earth, calcium carbonate, calcium sulfate, magnesium sulfate, magnesium oxide, magnesium carbonate, ground synthetic materials, fertilizers such as ammonium sulfate, ammonium phosphate, ammonium nitrate, apatite, zeolite, natural or synthetic silicic acid (e.g. silicic anhydride and synthetic calcium silicate); vegetable organic substances, such as nut shells (e.g. of walnuts or other nuts), soybean meal, tobacco powder, walnut powder, wheat flour, wood meal, starch and crystalline cellulose; synthetic or natural high molecular weight polymers, especially resins, such as cumarone resins, petroleum resins, alkyd resins, polyvinyl chloride, polyalkylene glycols, ketone resins, ester gums, xanthan gum, copal gum and dammar gum; waxes such as carnauba wax and beeswax, ureas, products of vegetable origin such as cereal meal, tree bark meal, wood meal and nutshell meal, cellulose powders, or other solid carriers. Alternatively granules can be made either by impregnating pellets of filler with the active ingredient or by pelleting a mixture of the active ingredient and powdered filler.

The compounds of the invention may also be in the form of dispersible powders, granules or grains. A water-dispersible granular formulation can be prepared by mixing the compounds of formula 1 or 1' or formula 5 or 5' or 5" with one or more additives selected from the group consisting of fillers, wet dispersing agents and binders, as described above in relation to the dust coating formulation, and then pulverizing the mixture. The pulverized mixture is then preferably added to an agitating fluidized bed granulator, water is added, and the whole is mixed and granulated, after which it is dried and sieved.

For wider applicability and labour saving, the composition of the invention can, if desired, be combined with one or more other pesticidal compounds or agrochemicals or growth stimulants, including for example, nematicides, insecticides, fungicides, herbicides, plant growth regulators, soil conditioners and fertilizers. The following known insecticidal and fungicidal compounds might be considered for use in such combination compositions:

(1) Insecticides, for example, include: larvicides and ovicides.
(2) Nematicides, for example, include: dinitrophenols, for example 2-methyl-4,6-dinitrophenol; and benzoylurea derivatives, for example N-(2,6-difluorobenzoyl)-N'-(4-chlorophenyl)urea.
(3) Fungicides, for example, include imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminum tris(ethyl phosphonate), DPX3217, ethirimol, dimethirimol, bupirimate, chlorothalonil, Chevron RE 20615, vinclozolin, procymidone, iprodione and metaxanine.

The above-mentioned carriers and various auxiliary agents may be used alone or in any desired combination, depending upon the type of preparation, the application and other factors. Similar factors will also be of importance in determining the concentration of the active compound in the formulation.

The plant growth regulating compounds of the present invention may be prepared for use by combining of formula 1 or 1' or formula 5 or 5' or 5" with one or more of the aforementioned agents by conventional means; for example, by simple mixing, if desired with other conventional ingredients, as described above, to give conventional agrochemical formulations.

The compounds of the present invention may be used in the control of weeds. In one form, parasitic weeds such as Striga may be prompted to germinate by application of the compounds of the present invention prior to the development of a host. Alternatively, weed seeds may be treated with compounds of the present invention and then eliminated with herbicides.

Generally, the compounds of formula 5, 5' or 5" show activity at extremely low concentrations. The concentrations of the compounds of formula 5, 5' or 5" in the ready-to-use preparations can be varied within wide ranges. In general, the formulations comprise from 0.000001 to 98% by weight, of at least one compound of formula 5, 5' or 5". The compounds of formula 5, 5' or 5" are employed in a purity of from 90% to 100%, preferably 95% to 100%.

As will be demonstrated in connection with certain examples in this specification, compounds of formula 5, 5' or 5" used in the method of the present invention have been found effective in regulating plant development in connection with a variety of plant species at a range of concentrations. Concentrations of as little as $1 \times 10^{-4}$ mg/L of compounds falling under the generic definition of formula 5, 5' or 5" have been observed to cause marked increase in germination of several varieties of plants. Moreover, compounds of formula 5, 5' or 5" used in the method of this invention, when employed at concentrations ranging from 10 mg/L to $1 \times 10^{-4}$ mg/L (or from 10 ppm to 100 ppt) have demonstrated pronounced modifications in plant development, including, but not limited to inducing germination of seeds.

The precise amount of the compound of formula 5, 5' or 5" will depend upon the particular plant species being treated. An amount of from about $1 \times 10^{-4}$ mg/L to as much as 10 mg/L of these compounds, when applied to a plant or plant material will result in responses depending upon the total amount of compound used, as well as the particular species which is being treated. The compounds used in the process of this invention are generally soluble in water. However, if desired, the compounds used in the process of this invention may be absorbed onto solid carriers such as vermiculite, attaclay, talc and the like for application via a granular vehicle. Application of water thin solutions or solids is accomplished using conventional equipment that is well known in the art.

Although the preferred method of application of the compounds used in the process of this invention is directly to the plant or plant material, it has been found that such compounds may be applied to the soil, and that such compounds will be seed-absorbed to a sufficient extent so as to result in responses in accordance with the teachings of this invention.

When treating seeds according to the present invention, seeds are contacted with the composition. Contacting seeds with the composition includes coating seeds or soaking seeds. Preferably, the seeds are contacted with the composition by coating. Seeds can be soaked in an aqueous solution containing a chemical composition of the invention. For example, seeds can be soaked for about 1 to about 24 hr (e.g. for at least 1 min, 5 min, 10 min, 20 min, 40 min, 80 min, 3 hr, 6 hr, 12 hr, 24 hr). Some types of seeds (e.g. soybean seeds) may be sensitive to moisture. Thus, soaking such seeds for an extended period of time may not be desirable. Seeds can be coated using a mixture of the chemical composition and melted gelatin or other commercially available materials such as polymers, clays, lime-based suspensions or other adhering materials. Alternatively, a mixture of the chemical composition and a paste derived from sticky rice can be used to coat seeds. Preferably, seeds coated using such a paste are planted very soon after coating. Such compositions are typically sprayed on the seeds, although other techniques can be used such as dip coating. Another method to coat seeds involves coating the inside wall of a round container with the composition, adding seeds, then rotating the container to cause the seeds to contact the wall and the composition (referred to herein as "container coating"). Seeds can be coated by combinations of coating methods. Whilst not intended to be limiting, the composition is still effective for up to 2 years after treatment.

In addition to the above methods of delivery, compounds of the invention may be sprayed directly onto the soil or mixed with seeds as they are delivered to the soil.

In yet another embodiment of the invention, there is provided a method for ascertaining whether a species of plant is responsive to said compounds, the method comprising the steps of:

(a) exposing a seed of the species of plant to a compound of formula (5); and
(b) measuring a response in the seed.

EXAMPLE FOR CARRYING OUT THE INVENTION

The following Examples serve to more fully describe the manner of using the above-described invention, as well as to set forth the best modes presently contemplated for carrying out various aspects of the invention. It is understood that these Examples in no way serve to limit the true scope of this invention, but rather are presented for illustrative purposes. One skilled in the art will appreciate that although specific reagents and conditions are outlined in the following examples, modifications can be made which are meant to be encompassed by the spirit and scope of the invention. The references cited herein are expressly incorporated by reference.

General Experimental

Melting points (m.p.) were determined using a Kofler hot-stage apparatus and are uncorrected. HPLC and UV absorbance data were obtained using an Agilent 1100 HPLC system with a photodiode array detector and an Agilent 1050 HPLC system equipped with a multiple wavelength detector. Separation was achieved as described in the methods. Semi-preparative HPLC was conducted using a Rainin HPLC system. IR spectra were recorded in $CH_2Cl_2$ solution using a Digilab Excalibur FTS 3000 spectrophotometer. GC-MS was conducted using an Agilent 6890 GC coupled with an Agilent 5973 mass spectrometer. High resolution mass spectra (HRMS) were recorded using a VG Autospec mass spectrometer using electron impact (EI, 70 eV) ionisation. $^1H$ and $^{13}C$ Nuclear magnetic resonance (NMR) spectra were recorded using a Bruker ARX-300, Bruker AV-500 or a Bruker AV-600 spectrometer. Chemical shifts are measured on the δ scale (in ppm) in $d_6$-acetone with residual acetone used as internal standard ($^1H$, δ 2.04 and $^{13}C$, δ 29.8). The signals are described as singlet (s), doublet (d), triplet (t), and quartet (q). Solvents used were of technical grade and were distilled before use. Millipore (MP) water was obtained by passage through a Milli-Q ultra-pure water system (Millipore, Australia).

Maltol, 2-chloropropionyl chloride and ethyl chloroacetate were obtained from Aldrich. Pyromeconic acid was prepared from Kojic acid (Merck) as described by Ellis et al. (1996).

Statistical Analyses

Data generated were statistically analysed by the Analysis of Variance (ANOVA). The original data expressed as a proportion (%) was transformed (arcsin √) to conform to ANOVA assumptions. Mean comparisons were made using Fisher's protected LSD, at the 95% confidence level (p<0.05) for all species except *Rhodocoma arida* where mean comparisons were made at the 92% confidence level (p<0.08).

Isolation of 3-methyl-2H-furo[2,3-c]pyran-2-one from smoke

Trapping of Smoke Chemical(s)

The smoke generated by burning 1000 Whatmans No. 1 filter paper (24 cm), which were torn into strips to aid combustion, was drawn from the combustion chamber (20 L drum) by reduced pressure, into a three-necked round bottom flask (5 L), through an air-cooled condenser and then bubbled through de-ionised (DI) water (1 L) (FIG. 1). A gas burner was used to heat the combustion chamber and an inlet of compressed air at the bottom was used to regulate the burning of the filter paper. The flask served as a 'trap' to condense the water produced from the combustion process, along with the majority of the smoke chemicals, including the active compound(s) in smoke. The more volatile smoke passed through the trap and into the DI water, thus ensuring maximum trapping of the volatile chemicals.

The trap and drum were washed out with water followed by ether to isolate the chemicals of interest and thus produce a greater concentration of the active compound compared to that obtained with smoke-water.

Generation of Plant-Derived Smoke Water

The smoke generated in a metal drum (60 L) by burning green and dry plant material (~6 kg) collected from native *Banksia-Eucalyptus* woodlands was drawn through 10 L of deionised water for one hour by suction. The resultant dark brown solution (termed plant-derived smoke water) was stored in a laboratory freezer (−18° C.) until use.

Extraction and Solvent Fractionation

The aqueous trap residue was extracted three times with ether (3×300 mL) and the combined organic extract was washed with 1M $NaHCO_3$ (3×200 mL) to remove the stronger acids (i.e. Carboxylic acids etc.) and 1 M NaOH (3×200 mL) to remove the weaker acids (i.e. Phenolic type compounds). The resulting ethereal solution was dried ($Na_2SO_4$), filtered and distilled (37° C., 1 atm) to yield the neutral fraction (trap ~9.8 g, drum ~2.5 g red/brown oil). Recovery of the $NaHCO_3$ and NaOH soluble extracts was achieved by acidification (2M HCl) and back extracting with ether. A sub-sample of each fraction was tested in the Grand Rapids bioassay and the *C. aculeata* bioassay where activity was shown to reside in the neutral fraction.

$C_{18}$ Fractionation

The neutral fraction (2 g) was added dropwise with the aid of a small portion of acetonitrile (ca. 0.2 mL) to a column containing C-18 silica (10 g Fluka Silica Gel 100 $C_{18}$—reversed phase) and eluted under reduced pressure (~20 mmHg) with MP water (50 mL) followed by 5% acetonitrile/water (50 mL); 10% acetonitrile/water (50 mL); 20% acetonitrile/water (50 mL); 50% acetonitrile/water (50 mL) and finally 100% acetonitrile (50 mL). A total of 6 fractions (50 mL) were collected and subjected to bioassay evaluation by taking a small aliquot (ca. 100 µL) and evaporating off the solvents under a stream of nitrogen. The aliquot was made up to 10 mL with MP water and diluted as required (typically 1/100). Germination promotion activity was shown to be associated with primarily the $2^{nd}$ fraction with some activity also present in the $3^{rd}$ fraction. The active fractions were then extracted with $CH_2Cl_2$ (3×20 mL) and the combined organic extracts were dried ($Na_2SO_4$), filtered and evaporated to dryness to yield light yellow oils (typical yields—Fraction 2 ~140 mg, Fraction 3 ~60 mg).

Preparative HPLC Separation

The active fractions from $C_{18}$ fractionation (~100 mg) were dissolved in acetonitrile (1 mL) and injected onto a semi-preparative HPLC column (250*22 mm Alltech Econosil $C_{18}$, 5 µm) and eluted with 20% acetonitrile/water at a flow rate of 20 mL/min and fractions were collected at 1 minute intervals (i.e. 20 mL) for 40 minutes and an aliquot of each subjected to bioassay evaluation as described above. Germination activity was confirmed for fractions corresponding to elution times between 18 and 24 minutes. The active fractions were extracted with $CH_2Cl_2$ (2×20 mL) and the combined organic extract was dried ($Na_2SO_4$), filtered and evaporated to dryness to yield light yellow oils (typically ~1-2 mg for each fraction). The active fractions were combined and subjected to further separation.

Asahipak HPLC Separation

Asahipak HPLC separation was achieved using an Asahipak reversed phase. HPLC column (250*4 mm Hewlett Packard Asahipak ODP-50, 5 µm) which was subjected to isocratic elution with 20% acetonitrile/water at a flow rate of 1 mL/min and 40 µL of the test solution (concentration ~5-10 mg/mL) was injected. Initially, 1-minute fractions were collected and subjected to bioassay evaluation to determine the retention time of the active compound. This was found to be between 14 and 16 minutes, which correlated well with a distinctive UV absorbance peak at 330 nm. Multiple injections were made and the active fraction was collected and combined from each injection. The combined fraction was extracted with $CH_2Cl_2$ (3×30 mL) and the combined organic extract was dried ($Na_2SO_4$), filtered and evaporated to dryness to yield a light yellow oil (5.4 mg). The fraction was then subjected to further separation.

$C_{18}$ HPLC Separation $C_{18}$ HPLC separation was achieved using a $C_{18}$ reversed phase column (250*4 mm Hewlett Packard Hypersil, 5 µm) and subjected to isocratic elution with 25% methanol/water at a flow rate of 1 mL/min and 40 µL of the test solution (5 mg/mL) was injected. The fraction showed that 3 main compounds were present and each compound was separated and collected to give fractions L-1, L-2 and L-3. The fractions were extracted as described above to yield light yellow oils (L-1~0.5 mg, L-2~1.3 mg and L-3~1.6 mg). A sample of each fraction was tested using the bioassays, which showed L-2 was the active compound (Table 1).

Seed Bioassays

Grand Rapids Bioassay

Grand Rapids Lettuce seeds (Waltham strain) were obtained from R.B. Dessert Seed Co. and were frozen in sachets until use. For testing of aqueous samples, 2.5 mL of test solution was applied to three replicates of 40-50 seeds in Petri dishes (90 mm) lined with two layers of Whatman No. 1 filter paper (7 cm). Millipore filtered water (MP water) was used as a control for each experiment and dilutions of each sample were used to ensure the optimum concentration range for activity. Fractions were reconstituted to their original concentration (before fractionation) and dilutions were made using MP water. Petri dishes were sealed with a layer of plastic wrap, and stored in a light proof container. All manipulations involving the seed were carried out in a dark room and germinants, based on the appearance of a radicle, were scored after 48 hours incubation.

Native Bioassays

*Conostylis aculeata* and *Stylidium affine* seeds were obtained from Nindethana seed service and stored before use. For testing of aqueous samples, three replicates of 20-30 sterilised seeds were added to UV sterilised petri dishes (90 mm), containing two Whatman No. 1 filter papers (7 cm) moistened with the filtered test solution (2.5 mL, 0.22 µm). MP water was used as a control for each experiment and dilutions of each sample were used to ensure the optimum concentration range for activity. Petri dishes were then sealed with parafilm and incubated in the dark at 20±1° C. The seeds were scored on a weekly basis with optimum germination achieved between 4-6 weeks.

For the soil-based germination trials, four replicates of 25 seeds were soaked in the test solution (water (control) or compound 1 analogues at 10 ppb) for 24 hours, dried in a laminar flow cabinet and sowed in a germination mix. The soil-sown seeds were incubated in the dark at 20±1° C. and were scored on a weekly basis.

Seed Vigour Enhancement

For each species, five replicates of 20 seeds were placed on Petri dishes lined with seed germination paper. The Petri dishes were moistened with de-ionised water (control) or 100 ppb compound 1a. All species were incubated in constant darkness at 12/12 hr alternating temperatures of 7/18° C., 13/26° C. or 18/33° C. Germination was scored on radicle emergence and was recorded every 2-3 days until germination had ceased.

Weed Germination Enhancement

For each species, four replicates of 25 seeds were placed on Petri dishes lined with seed germination paper. The Petri dishes were moistened with de-ionised water (control) or 100 ppb compound 1a. All species were incubated in constant darkness at 12/12 hr alternating temperatures of 7/18° C., 13/26° C. or 18/33° C. Germination (radicle emergence) was recorded every 2-3 days until germination had ceased.

Germination Enhancement of Species Used in Amenity Horticulture

For each species, three replicates of 25 seeds were placed on Petri dishes lined with seed germination paper. The Petri dishes were moistened with de-ionised water (control) or 100 ppb compound 1a. All species were incubated in constant darkness at 18° C. Germination (radicle emergence) was recorded five times a week.

Germination Enhancement of Species Used in Rangeland Pasture Systems

Three replicates of 25 seeds were placed on Petri dishes lined with seed germination paper. The Petri dishes were moistened with de-ionised water (control) or 100 ppb compound 1a. All species were incubated in constant darkness at 18° C. Germination (radicle emergence) was recorded every 2-3 days until germination had ceased.

Effective Delivery Systems for Compound 1a

Seed Coating

Seeds were coated by a commercial coating company (Pioneer Hi-Bred Australia Pty Ltd) using a film-coating process or a polymer build-up coating process.

Seeds were coated without compound 1a (control), or with 100 ppb compound 1a added at a rate of 3 mL per 10 g seeds. Four replicates of 50 coated seeds were sown in punnets containing a standard nursery soil mix. The punnets were kept continually moist and incubated at 17° C. Seedling emergence was every 2-3 days until germination had ceased.

Seed Priming

For testing on Australian species, three replicates of 25 seeds were soaked in one of de-ionised DI water or 100 ppb compound 1a for 24 hr at 23° C. The seeds were re-dried at 23° C. for 24 hr and incubated on Petri dishes containing 0.7% (w/v) water agar in constant darkness at 18° C. Germination (radicle emergence) was recorded every 2-3 days until germination had ceased.

To determine the duration of priming required to induce a germination response, three replicates of 20 seeds of *Emmenanthe penduliflora* were soaked in at 23° C. in a 100 ppb compound 1a solution for 1, 5, 10, 20, 40 or 80 min or 3, 6, 12, 24 or 48 hr. The seeds were re-dried for 24 hr at 23° C. and placed on Petri dishes lined with seed germination paper and moistened with de-ionised water. The Petri dishes were incubated at 18° C. in constant darkness. Germination (radicle emergence) was recorded every 2-3 days until germination had ceased.

Compound 1a as a Replacement for Other Dormancy Release Agents

Compound 1a as a Replacement for Light or Gibberellic Acid

Three replicates of 50 seeds of *Podolepis canescens* were placed on Petri dishes containing filter paper moistened with de-ionised water (control), 1, 10 or 100 ppb compound 1a or 1000 ppm gibberellic acid. The Petri dishes were incubated at 12/12 hr alternating temperatures of 7/18° C., 13/26° C. or 18/33° C. and incubated in white light or continuous darkness. All of the treatments were added to the Petri dishes in complete darkness prior to moving to the incubators. Germination was recorded following 7 days incubation.

Compound 1a as a Replacement for De-Hulling of Grass Species

Intact or de-hulled seeds were employed for this experiment. Seeds were de-hulled manually by carefully extracting the seeds from the surrounding palea and lemma. Three replicates of 25 intact or de-hulled seeds were placed on Petri dishes lined with seed germination paper. The Petri dishes were moistened with de-ionised water (control) or 100 ppb compound 1a. All species were incubated in constant darkness at 18° C. Germination (radicle emergence) was recorded every 2-3 days until germination had ceased.

Compound 1a Stimulation of Germination in Nutriceutically Important Plants.

Three replicates of 25 seeds were placed on Petri dishes lined with seed germination paper. The Petri dishes were moistened with de-ionised water (control), 10 or 100 ppb compound 1a. Seeds were incubated in constant darkness at 18° C. Germination (radicle emergence) was recorded every 2-3 days until germination had ceased.

Reactivity of Compound 1a with Somatic Tissue

Seedling Coleoptiles

Seeds were cultured on PGR-free 1/2 MS medium for 4 weeks in darkness, then 3 mm coleoptile sections were removed under aseptic conditions and explanted to culture media supplemented with 1 or 2 mM 2,4-dichlorophenoxyacetic acid and compound 1a (0, 1.0, 10, 100 ppb, respectively), with incubation in darkness at 22-25° C. Each plate was inoculated with 10 coleoptile sections and every treatment was replicated by 6 plates. Induction of callus and somatic embryogenesis was observed at various intervals.

In Vitro-Grown Shoots

Shoots of Baloskion tetraphyllum were cultured on 1/2 MS basal medium supplemented with 1 mM BAP in 16 hr light culture (PPFD of 30 $\mu molm^{-2}s^{-1}$).

After two months, whole shoots were trimmed of upper leaf and basal roots to 4 mm in length, then explanted to culture media with 1 mM 2,4-dichlorophenoxyacetic acid and supplemented with different concentrations of compound 1a (0, 1.0, 10, 100 ppb, respectively) and incubated in darkness at 22-25° C. Each plate was inoculated with 10 trimmed shoots and every treatment replicated with 4 plates. Somatic embryogenesis and plant regeneration was investigated at various intervals.

Germination Results of L-fractions

From Table 1, it is apparent that L-2 promoted the germination of all three species of seed significantly higher than that of the control (water). However, L-1 and L-3 failed to give any enhancement of germination. Given the similarities between the 3 compounds (i.e. UV absorbance, Mass spectrum, molecular formula) we attempted to identify each compound as an aid to identifying the active compound, L-2.

TABLE 1

Germination results of the 3 compounds isolated from smoke.

| | Grand Rapids | *Conostylis aculeata* | *Stylidium affine* |
|---|---|---|---|
| Control (MP water) | 39.5 (4.5) | 17.1 (3.4) | 0 |
| L-1 | 42.4 (6.6) | 7.5 (1.3) | 0 |
| L-2 | 99.3 (0.7) | 46.5 (4.9) | 67.9 (2.5) |
| L-3 | 42.1 (1.5) | 11.6 (2.5) | 0 |

Note:
Values indicate mean germination percentages and parenthesis values indicate standard errors of the mean (SEM).

Identification of the Compounds Present in the L-Fractions

The compound in fraction L-1 was identified as 2,3'-bifuran-5'(2'H)-one by comparison with literature data (Wu et al., 2003).

The compound in fraction L-2 was also unknown in the chemical literature and was tentatively identified as 3-methyl-2H-furo[2,3-c]pyran-2-one (1a). The structure of L-2 was later confirmed by synthesis.

The compound in fraction L-3 was found to be unknown in the chemical literature and was identified as 7-methyl-5H- furo[3,2-b]pyran-5-one, by comparison with the similar known compound, 2,7-dimethyl-5H-furo[3,2-b]pyran-5-one (Rautenstrauch et al., 1989).

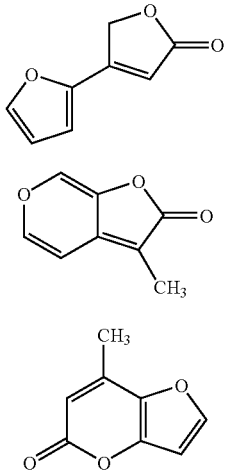

Chemical structures of the three isolated compounds from smoke. Each compound has a molecular formula of $C_8H_5O_3$.

Spectroscopic Data

L-1: $^1$H NMR (500.1 MHz, $d_6$-acetone): δ 7.85 (1H, d, J=1.8 Hz, H-5); 7.09 (1H, d, J=3.5 Hz, H-3); 6.68 (1H, dd, J=3.5,1.8 Hz, H-4); 6.21 (1H, t, J=1.8 Hz, H-4'); 5.21 (2H, d, J=1.8 Hz, H-2'). $^{13}$C NMR (125.8 MHz, $d_6$-acetone): δ 173.8 (C=O); 153.9 (C-3'); 147.2 (C-5); 147.0 (C-2); 114.8 (C-3); 113.4 (C-4); 110.3 (C-4'); 70.2 (C-2'). GC-MS (EI): 150 (M$^+$, 100), 121 (63), 93 (15), 92 (46), 65 (16), 63 (15). UV (25% MeOH/H$_2$O) $\lambda_{max}$: 302 nm.

L-2: $^1$H NMR (500.1 MHz, $d_6$-acetone): δ 7.78 (1H, s, H-7); 7.63 (1H, d, J=5.5 Hz, H-5); 6.79 (1H, d, J=5.5 Hz, H-4); 1.88 (3H, s, CH$_3$). $^{13}$C NMR (125.8 MHz, $d_6$-acetone): δ 171.1 (C=O); 149.8 (C-5); 143.0 (C-7a); 140.6 (C-3a); 128.0 (C-7); 104.1 (C-4); 100.0 (C-3); 7.5 (CH$_3$). GC-MS (EI): 150 (M$^+$, 100), 122 (25), 121 (71), 66 (14), 65 (16). UV (HPLC-DAD, 25% MeOH/H$_2$O) $\lambda_{max}$: 332 nm, 320 nm.

L-3: $^1$H NMR (500.1 MHz, $d_6$-acetone): δ 7.9 (1H, dd, J=2.2, 0.5 Hz, H-2); 6.73 (1H, d, J=2.2 Hz, H-3); 5.92 (1H, dq, J=1.2, 0.5 Hz, H-6); 2.37 (3H, d, J=1.2 Hz, CH$_3$) $^{13}$C NMR (125.8 MHz, $d_6$-acetone): δ 162.0 (C=O); 148.2 (C-3a); 147.6 (C-2); 145.9 (C-7); 138.4 (C-7a); 108.0 (C-6); 103.9 (C-3); 15.3 (CH$_3$). GC-MS (EI): 150 (M$^+$, 100), 122 (56), 121 (49), 68 (16), 66 (13). UV (25% MeOH/H$_2$O) $\lambda_{max}$: 331 nm. IR (CH$_2$Cl$_2$): 1724 cm$^{-1}$ (C=O).

Synthesis of L-2 (i.e. 1a)

3-Hydroxy-4H-pyran-4-one (6) (Pyromeconic acid) was prepared from the readily available Kojic acid following the method of Ellis et al., (1996)

Method A

The following depicts a general scheme for synthesis of 3-methyl-2H-furo[2,3-c]pyran-2one (1a) from Pyromeconic acid (6) termed method A.

Scheme 1. General synthetic scheme for the synthesis of 3-methyl-2H-furo[2,3-c]pyran-2-one (1a).

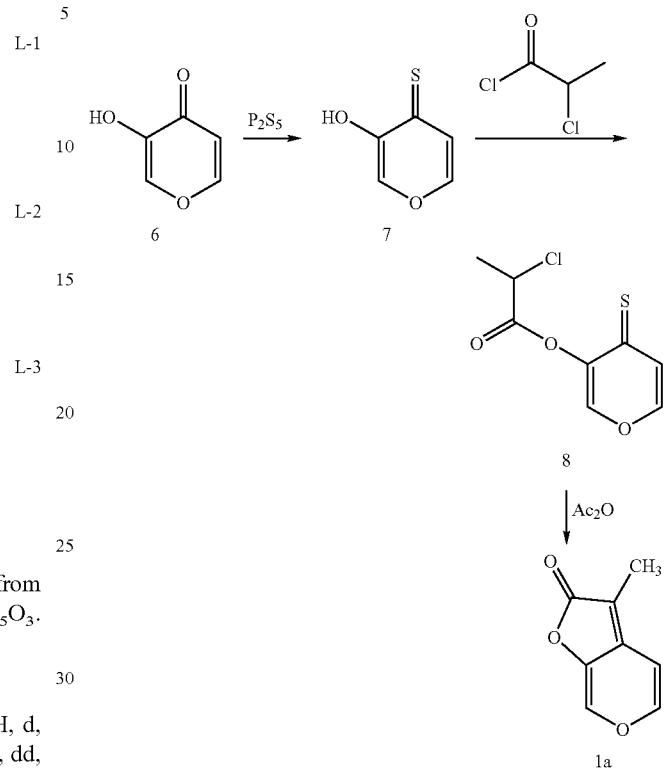

3-Hydroxy-4H-pyran-4-thione (7) Phosphorus pentasulphide (1.16 g, 5.2 mmol) in tetrahydrofuran was added to a stirred solution of pyromeconic acid (6) (390 mg, 3.5 mmol) in tetrahydrofuran (10 mL). Solid sodium-hydrogen carbonate (1.7 g, 20.2 mmol) was added and the reaction mixture stirred for 2 hr at room temperature. The orange reaction mixture was poured into water (100 mL) and extracted with ethyl acetate (3×20 mL). The combined organic extracts were washed with brine, dried (Na$_2$SO$_4$), filtered and evaporated to dryness to yield a red/orange residue. The residue was purified by rapid silica filtration (30% ethyl acetate/hexane) to give 7 as an orange oil, which solidified on cooling (260 mg, 58%). 7: $^1$HNMR ($d_6$-acetone): δ 8.21 (1H, s); 8.03 (1H, d, J=5 Hz); 7.85 (1H, br s); 7.46 (1H, d, J=5 Hz). $^{13}$CNMR ($d_6$-acetone): δ 189.3(s); 153.9 (s); 150.1 (d); 135.4 (d); 125.7 (d).

4-Thioxo-4H-pyran-3-yl 2-chloropropanoate (8). Solid potassium carbonate (332 mg, 2.4 mmol) was added to a solution of 7 (156 mg, 1.2 mmol) in acetone (10 mL) and stirred for 5 minutes. A solution of 2-chloropropionyl chloride (305 mg, 2.4 mmol) diluted in acetone was added and the reaction mixture stirred at room temperature for 2 hr. The inorganic material was removed by filtration and the filtrate evaporated to dryness to give a red/orange residue. The residue was dissolved in dichloromethane (30 mL), washed with 0.2M potassium carbonate solution (20 mL), brine and the organic extract dried (Na$_2$SO$_4$), filtered and evaporated to dryness to give 8 as a red oil, which solidified on cooling (195 mg, 73%).

8: $^1$HNMR (d6-acetone): δ 8.35 (1H, s); 7.96 (1H, d, J=5.2 Hz); 7.32 (1H, d, J=5.2 Hz); 4.87 (1H, q, J=6.9 Hz); 1.81 (3H, t, J=6.9 Hz). $^{13}$CNMR (d6-acetone): δ 193.7 (s); 167.5 (s); 150.0 (s); 149.0 (d); 145.2 (d); 129.3 (d); 53.2 (d); 22.2 (q).

3-Methyl-2H-furo[2,3-c]pyran-2-one (1a). Solid sodium acetate (20 mg, 0.24 mmol) was added to a solution of 8 (23.4 mg, 0.11 mmol) in acetic anhydride (6 mL) and the resulting mixture heated at 120° C. for 3 hr. After cooling, water (15 mL) was added and the mixture was warmed gently to effect hydrolysis of the solvent. The light yellow solution was filtered and extracted with dichloromethane (3×20 mL). The organic extract was dried (Na$_2$SO$_4$), filtered and evaporated to dryness to give a residue containing mostly the acetyl ester (4-thioxo-4H-pyran-3-yl acetate) and some of 1a. The residue was dissolved in 0.2M potassium carbonate solution (50 mL) by heating gently and the resultant solution was filtered and extracted with dichloromethane (3×20 mL). The organic extract was dried (Na$_2$SO$_4$), filtered and evaporated to dryness to give a yellow residue (3.6 mg, 22%), which was recrystallised from hexane to afford 1a as light yellow needles (2 mg, 12%): mp 118-119° C.

1a: $^1$HNMR (d6-acetone): δ 7.77 (1H, s); 7.62 (1H, d, J=5.5 Hz); 6.79 (1H, d, J=5.5 Hz); 1.86 (3H, s). $^{13}$CNMR (d6-acetone): δ 171.1 (s); 149.8 (d); 143.0 (s); 140.6 (s); 128.0 (d); 104.1 (d); 100.0 (s); 7.6 (q).

Method B

The following depicts an alternate general scheme for synthesis of 3-methyl-2H-furo[2,3-c]pyran-2-one (1a) from Pyromeconic acid (6). This scheme follows the same chemical reactions depicted in scheme 1 and is termed method B.

3-Hydroxy-4H-pyran-4-thione (7). Phosphorus pentasulphide (1.5 g, 6.7 mmol) in tetrahydrofuran (2 mL) was added to a stirred solution of Pyromeconic acid (6) (500 mg, 4.5 mmol) in tetrahydrofuran (10 mL). Solid sodium-hydrogen carbonate (2.25 g, 26.8 mmol) was added and the reaction mixture stirred for 3 hr at room temperature. The orange reaction mixture was poured into water (50 mL) and extracted with ethyl acetate (3×20 mL). The combined organic extract was washed with brine, dried (Na$_2$SO$_4$), filtered and evaporated to dryness to yield a red/orange residue. The residue was purified by rapid silica filtration (30% ethyl acetate/hexane) to give 7 as an orange oil, which solidified on standing (385 mg, 67%).

7: $^1$H NMR (500.1 MHz, d$_6$-acetone): δ 8.21 (1H, s, H-2); 8.03 (1H, d, J=5.0 Hz, H-6); 7.85 (1H, br s, OH); 7.46 (1H, d, J=5.0 Hz, H-5). $^{13}$C NMR (125.8 MHz, d$_6$-acetone): δ 189.3 (C=S); 153.9 (C-3); 150.1 (C-6); 135.4 (C-2); 125.7 (C-5). HRMS calcd for C$_5$H$_4$O$_2$S 127.9932, found 127.9937.

4-Thioxo-4H-pyran-3-yl 2-chloropropanoate (8). Triethylamine (190 mg, 1.9 mmol) was added to a stirred solution of 7 (200 mg, 1.6 mmol) in dichloromethane (10 mL) at 0° C. A solution of 2-chloropropionyl chloride (240 mg, 1.9 mmol) diluted in dichloromethane (1 mL) was added dropwise and the reaction mixture stirred at 0° C. for 10 min. The red solution was evaporated to dryness in vacuo and the resulting residue was purified by rapid silica filtration (dichloromethane) to give 8 as a red oil (270 mg, 79%).

8: $^1$H NMR (500 MHz, d$_6$-acetone): δ 8.35 (1H, s, H-2); 7.96 (1H, d, J=5.2 Hz, H-6); 7.32 (1H, d, J=5.2 Hz, H-5); 4.87 (1H, q, J=6.9 Hz, CH$_2$); 1.81 (3H, t, J=6.9 Hz, CH$_3$). $^{13}$C NMR (125.8 MHz, d$_6$-acetone): δ 193.7 (C=S); 167.5 (C=O); 150.0 (C-3); 149.0 (C-6); 145.2 (C-2); 129.3 (C-5); 53.2 (CH); 22.2 (CH$_3$). HRMS calcd for C$_8$H$_7$O$_3$ClS 217.9804, found 217.9815.

3-methyl-2H-furo[2,3-c]pyran-2-one (1a) A mixture of anhydrous sodium acetate (280 mg, 3.4 mmol) and triphenyl phosphine (330 mg, 1.3 mmol) in acetic anhydride was heated at 140° C. for 5 min. A solution of 8 (250 mg, 1.1 mmol) diluted with acetic anhydride (2 mL) was added dropwise to the heated mixture. The mixture was heated for a further 30 minutes and allowed to cool. The dark mixture was poured into ice/water (100 mL) and stirred until one phase was formed. The aqueous solution was filtered and extracted with dichloromethane (3×20 mL). The organic extract was washed with 1 M NaHCO$_3$ (2×20 mL), dried (Na$_2$SO$_4$), filtered and evaporated to dryness. The residue was extracted with 0.2 M potassium carbonate solution (2×50 mL) by heating gently and the resulting yellow solution was filtered and extracted with dichloromethane (3×15 mL). The organic extract was washed with brine, dried (Na$_2$SO$_4$), filtered and evaporated to dryness to give a yellow residue, which was purified by silica gel chromatography (30% ethyl acetate/light petroleum) to afford 1a as a light yellow solid (38 mg, 22%).

1a: $^1$H NMR (500 MHz, d$_6$-acetone): δ 7.77 (1H, s, H-7); 7.62 (1H, d, J=5.5 Hz, H-5); 6.79 (1H, d, J=5.5 Hz, H-4); 1.86 (3H, s, CH$_3$). $^{13}$C NMR (125.8 MHz, d$_6$-acetone): δ 171.1 (C=O); 149.8 (C-5); 143.0 (C-7a); 140.6 (C-3a); 128.0 (C-7); 104.1 (C-4); 100.0 (C-3); 7.6 (CH$_3$). HRMS calculated for C$_8$H$_6$O$_3$ 150.0317, found 150.0320. mp: 118-119° C. UV (λ$_{max}$ in nm, log ε): 347 (3.99), 330 (4.27), 320 (4.27), 242 (3.49), 202 (4.00). IR (CH$_2$Cl$_2$): 1746 cm$^{-1}$ (C=O).

Preparation of 2H-furo[2,3-c]pyran-2-one (1b)

1b

Prepared from Pyromeconic acid (Ellis et al., 1996) using method B and 2-chloroacetyl chloride as the esterifying agent.

1b: $^1$H NMR (300.1 MHz, d$_6$-acetone): δ 7.92 (1H, d, J=1.5 Hz, H-7); 7.70 (1H, d, J=5.4 Hz, H-5); 6.90 (1H, dd, J=5.4, 0.5 Hz, H-4); 5.40 (1H, dd, J=1.5, 0.5 Hz, H-3). $^{13}$C NMR (75.5 MHz, d$_6$-acetone): δ 170.5 (C=O); 151.1 (C-5); 146.1 (C-3a); 144.1 (C-7a); 129.4 (C-7); 105.5 (C-4); 90.7 (C-3). HRMS calculated for C$_7$H$_4$O$_3$ 136.0160, found 136.0164.

Preparation of 7-methyl-2H-furo[2,3-c]pyran-2-one (1c)

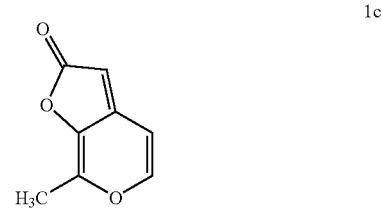

1c

Prepared from Maltol using method B and 2-chloroacetyl chloride as the esterifying agent.

1c: $^1$H NMR (600.1 MHz, d$_6$-acetone): δ 7.67 (1H, d, J=5.4 Hz, H-5); 6.82 (1H, d, J=5.4 Hz, H-4); 5.34 (1H, s, H-3); 2.36 (1H, s, CH$_3$). $^{13}$C NMR (150.9 MHz, d$_6$-acetone): δ 170.6 (C=O); 150.7 (C-5); 146.0 (C-3a); 140.2 (C-7a); 138.9 (C-7); 105.1 (C-4); 90.1 (C-3); 14.0 (CH$_3$). HRMS calculated for C$_8$H$_6$O$_3$ 150.0317, found 150.0314.

Preparation of 5-methyl-2H-furo[2,3-c]pyran-2-one (1d)

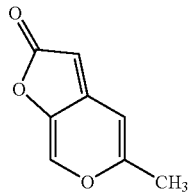

1d

Prepared from Allomaltol (Ellis et al., 1996) using method B and 2-chloroacetyl chloride as the esterifying agent.

1d: $^1$H NMR (600.1 MHz, $d_6$-acetone): δ 7.84 (1H, d, J=1.4 Hz, H-7); 6.67 (1H, q, J=0.7 Hz, H-4); 5.26 (1H, d, J=1.4 Hz, H-3); 2.32 (1H, d, J=0.7 Hz, $CH_3$). $^{13}$C NMR (150.9 MHz, $d_6$-acetone): δ 170.9 (C=O); 161.3 (C-5); 147.8 (C-3a); 143.4 (C-7a); 128.9 (C-7); 102.6 (C-4); 89.2 (C-3); 14.0 ($CH_3$). HRMS calculated for $C_8H_6O_3$ 150.0317, found 150.0312

Preparation of 3,7-dimethyl-2H-furo[2,3-c]pyran-2-one (1e)

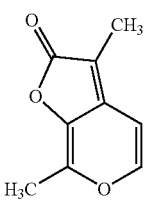

1e

Prepared from Maltol Using Method A.

1e: $^1$H NMR (500.1 MHz, $d_6$-acetone): δ 7.59 (1H, d, J=5.5 Hz, H-5); 6.73 (1H, d, J=5.5 Hz, H-4); 2.32 (1H, s, $CH_3$); 1.84 (1H, s, $CH_3$). $^{13}$C NMR (125.8 MHz, $d_6$ acetone): δ 171.2 (C=O); 149.6 (C-5); 140.8 (C-3a); 138.9 (C-7a); 137.3 (C-7); 103.7 (C-4); 99.4 (C-3); 13.8 ($CH_3$); 7.7 ($CH_3$). HRMS calculated for $C_9H_8O_3$ 164.0473, found 164.0478.

Preparation of 3,5-dimethyl-2H-furo[2,3-c]pyran-2-one (1f)

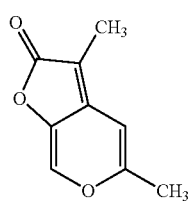

1f

Prepared from Allomaltol (Ellis et al., 1996) using method A.

1f: $^1$H NMR (500.1 MHz, $d_6$-acetone): δ 7.71 (1H, s, H-7); 6.58 (1H, s, H-4); 2.28 (3H, s, $CH_3$), 1.83 (3H, s, $CH_3$). $^{13}$C NMR (125.8 MHz, $d_6$-acetone): δ 171.5 (C=O); 159.9 (C-5); 142.4 (C-3a); 142.4 (C-7a); 127.7 (C-7); 101.1 (C-4); 98.4 (C-3); 19.8 ($CH_3$); 7.5 ($CH_3$). HRMS calculated for $C_9H_8O_3$ 164.0473, found 164.0476.

Preparation of 3,5,7-trimethyl-2H-furo[2,3-c]pyran-2-one (1g)

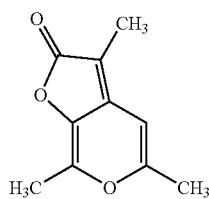

1g

Prepared from 3-hydroxy-2,6-dimethyl-4H-pyran-4-one (Ellis et al., 1996) using method B.

1g: $^1$H NMR (600.1 MHz, $d_6$-acetone): δ 6.49 (1H, s, H-4); 2.28 (3H, s, $CH_3$); 2.27 (3H, s, $CH_3$); 1.79 (3H, s, $CH_3$). $^{13}$C NMR (150.9 MHz, $d_6$-acetone): δ 171.5 (C=O); 159.5 (C-5); 142.4 (C-7a); 138.2 (C-7); 136.7 (C-3a); 100.7 (C-4); 97.8 (C-3); 19.7 ($CH_3$); 13.8 ($CH_3$); 7.6 ($CH_3$). HRMS calculated for $C_{10}H_{10}O_3$ 178.0630, found 178.0629.

Preparation of 5-methoxymethyl-3-methyl-2H-furo[2,3-c]pyran-2-one (1h)

1h

Prepared from 3-hydroxy-6-(methoxymethyl)=4H-pyran-4-one (Ellis et al., 1996) using method B.

1h: $^1$H NMR (600.1 MHz, $d_6$-acetone): δ 7.75 (1H, s, H-7); 6.78 (1H, q, J=0.8 Hz, H-4); 4.27 (2H, d, J=0.8 Hz, $CH_2$); 3.40 (3H, s, $OCH_3$); 1.87 (3H, s, $CH_3$). $^{13}$C NMR (150.9 MHz, $d_6$-acetone): δ 171.3 (C=O); 158.8 (C-5); 142.6 (C-7a); 141.4 (C-3a); 127.6 (C-7); 101.3 (C-4); 100.3 (C-3); 71.0 ($CH_2$); 58.8 ($OCH_3$); 7.6 ($CH_3$). HRMS calcd for $C_{10}H_{10}O_4$ 194.0579, found 194.0586.

Preparation of 4-bromo-3,7-dimethyl 2H-furo[2,3-c]pyran-2-one (1i)

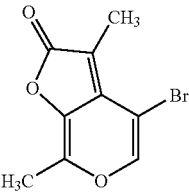

1i

Prepared from bromomaltol (Looker et al., 1979) using method B.

1i: $^1$H NMR (500.1 MHz, $d_6$-acetone): δ 7.85 (1H, s, H-5); 2.32 (1H, s, $CH_3$); 2.07 (1H, s, $CH_3$). $^{13}$C NMR (125.8 MHz, $d_6$-acetone): δ 170.7 (C=O); 148.5 (C-5); 138.2 (C-3a); 137.7 (C-7); 137.2 (C-7a); 102.4 (C-3); 100.3 (C-4); 13.7 ($CH_3$); 8.3 ($CH_3$). HRMS calcd for $C_9H_7BrO_3$ 241.9579, found 241.9570.

Preparation of 3-methylfuro[2,3-c]pyridin-2(3H)-one (1j)

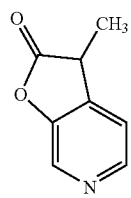
1j

Prepared from 1a with concentrated ammonium hydroxide solution following the method described by Hwang et al. (1980).

1j: $^1$H NMR (600.1 MHz, $d_6$-acetone): δ 8.14 (1H, s, H-7); 7.97 (1H, d, J=4.9 Hz, H-5); 7.05 (1H, d, J=4.9 Hz, H-4); 3.90 (1H, q, J=7.2 Hz, H-3); 1.48 (3H, d, J=7.2 Hz, $CH_3$). $^{13}$C NMR (150.9 MHz, $d_6$-acetone): δ 178.7 (C=O); 153.3 (C-7a); 142.0 (C-5); 140.9 (C-7); 135.2 (C-3a); 124.3 (C-4); 44.6 (C-3); 17.4 ($CH_3$). HRMS calculated for $C_8H_7NO_2$ 149.0477, found 149.0479.

Preparation of 3,6-dimethylfuro[2,3-c]pyridin-2(6H)one (1k)

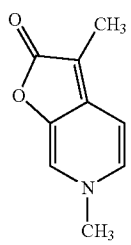
1k

Prepared from 1a with 24% aqueous methylamine solution following the method described by Liu et al. (2001).

1k: $^1$H NMR (600.1 MHz, $d_6$-acetone): δ 7.38 (1H, dd, J=6.9, 1.4 Hz, H-5); 7.32 (1H, d, J=1.4 Hz, H-5); 6.54 (1H, d, J=6.9, H-4); 3.81 (3H, s, N—$CH_3$); 1.79 (3H, s, $CH_3$). $^{13}$C NMR (150.9 MHz, $d_6$-acetone): δ 172.0 (C=O); 144.2 (C-3a); 143.7 (C-7a); 135.8 (C-5); 114.5 (C-7); 103.3 (C-4); 86.0 (C-3); 44.1 (N—$CH_3$); 7.4 ($CH_3$). HRMS calcd for $C_9H_9NO_2$ 163.0633, found 163.0628.

Preparation of ethyl 2-(4H-pyran-4-ylidene) acetate (5a) and ethyl 2-(acetylthio)-2-(4H-pyran-4-ylidene) acetate (5b)

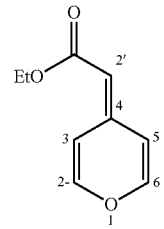
5a

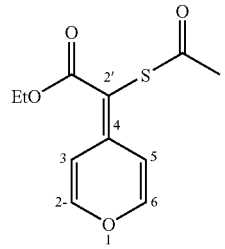
5b 4H-pyran-4-thione (108 mg, 1 mmol) (Okhata et al., 1986) was added to a mixture of anhydrous sodium acetate (164 mg, 2 mmol) and triphenyl phosphine (289 mg, 1.1 mmol) in acetic anhydride (5 mL). The resulting mixture was heated at 140° C. for 5 min. Ethyl chloroacetate (245 mg, 2 mmol) diluted with acetic anhydride (ca. 1 mL) was added dropwise to the heated mixture. The mixture was heated for three hours and allowed to cool. The dark mixture was poured into ice/water (100 mL) and stirred until one phase was formed. The aqueous solution was filtered and extracted with dichloromethane (3×20 mL). The organic extract was washed with 1 M $NaHCO_3$ (2×20 mL), dried ($Na_2SO_4$), filtered and evaporated to dryness to yield an oily residue. The crude residue was purified by silica gel chromatography using 10% ethyl acetate/light petroleum as eluent to yield 5a (3.5 mg, 0.2 mmol, 2%) and 20% ethyl acetate/light petroleum to give 5b (123 mg, 0.51 mmol, 51%).

5a: $^1$H NMR (300.1 MHz, $d_6$-acetone): δ 7.52 (1H, m, H-2 or H-6); 7.17-7.20 (2H, m, H-2 or H-6 and H-3 or H-5); 6.14 (1H, m, H-3 or H-5); 5.05 (1H, m, H-2'); 4.05 (2H, q, J=7.1 Hz, $CH_2$); 1.19 (3H, t, J=7.1 Hz, $CH_3$). $^{13}$C NMR (75.5 MHz, $d_6$-acetone): δ 167.8 (C=O); 148.8, 148.3 (C-2, C-6); 142.1 (C-4); 113.4, 109.6 (C-3, C-5); 99.5 (C-2'); 59.2 ($CH_2$); 14.7 ($CH_3$).

5b: $^1$H NMR (300.1 MHz, $d_6$-acetone): δ 7.89 (1H, m, H-2 or H-6); 7.43-7.45 (2H, m, H-2 or H-6 and H-3 or H-5); 6.72 (1H, m, H-3 or H-5); 4.11 (2H, q, J=7.1 Hz, $CH_2$); 2.31 (3H, s, $SCOCH_3$); 1.20 (3H, t, J=7.1 Hz, $CH_3$). $^{13}$C NMR (75.5 MHz, $d_6$-acetone): δ 194.1 (SC=O); 166.6 (C=O); 150.3, 149.8 (C-2, C-6); 146.7 (C-4); 112.0, 111.5 (C-3, C-5); 97.6 (C-2'); 60.7 ($CH_2$); 14.5 ($CH_3$). HRMS calculated for $C_{11}H_{12}O_4S$ 240.0456, found 240.0463.

Preparation of 2-(2,6-dimethyl-4H-pyran-4-ylidene)-1-phenylethanone (5c)

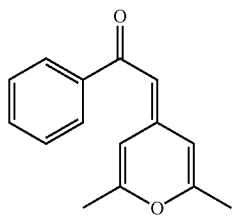

Prepared according to Okhata et al. (1986). All spectral data was identical to those reported in the literature.

Preparation of 2-(2,6-dimethyl-4H-pyran-4-ylidene)-1-phenylethanone (5d)

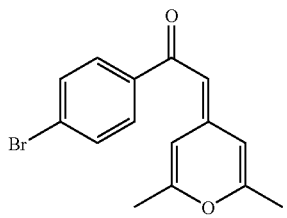

Prepared according to Okhata et al., (1986). All spectral data was identical to those reported in the literature.

Germination Results of the Synthetic Compound 1a

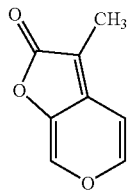

The synthetic compound 1a (3-Methyl-2H-furo[2,3-c]pyran-2-one) was tested using the Grand Rapids bioassay. As a comparison, plant-derived smoke water (SW) was also tested at a range of dilutions to give an indication of the relative concentration of 1a, which is likely to be present in smoke water (Table 2.).

The germination results (Table 2 and FIG. 2) show that compound 1a promotes the germination of Grand Rapids to the same level as smoke water. An estimate of the concentration of compound 1a in smoke water can be drawn from these results based on the decreasing promotion of germination of both the smoke water and the synthetic compound 1a. That is, the germination of 1/100 smoke water is roughly equivalent to 0.1 μg/L of compound 1a (i.e. 1/10 000 dilution) and at higher dilution, promotion of germination decreases for both the smoke water and compound 1a. Therefore, a relative concentration of compound 1a in neat smoke water is approximately 10 ppb (10 μg/L, $6.7 \times 10^{-8}$ mol/L) and is active at a 1/100 dilution of this initial concentration (i.e. 1 mg per 10 000 L, active at levels of $10^{-10}$ mol/L). Furthermore, at higher concentrations of 1a compared to the amount in smoke water, no inhibition of germination is observed. Hence, the inhibition of germination observed for neat smoke water is due to other compounds in smoke water and not compound 1a.

TABLE 2

Grand Rapids germination of 1a compared to smoke water (SW). Presented graphically in FIG. 2.

| | Plant-derived SW | Compound 1a (1 mg/L) |
|---|---|---|
| Neat | 34.9 (2.4) | 99.4 (0.6) |
| 1/10 dilution | 94.0 (2.0) | 98.4 (0.9) |
| 1/100 dilution | 90.1 (1.2) | 98.4 (1.6) |
| 1/1000 dilution | 76.8 (1.6) | 97.0 (0.5) |
| 1/10000 dilution | 60.8 (1.7) | 96.4 (0.6) |
| 1/100000 dilution | N/A | 76.9 (1.5) |
| 1/1000000 dilution | N/A | 60.9 (2.5) |

Note: Values indicate mean germination percentages and parenthesis values indicate standard errors of the mean. Control (MP water) germination was 51% (1.8).

Figure 2:
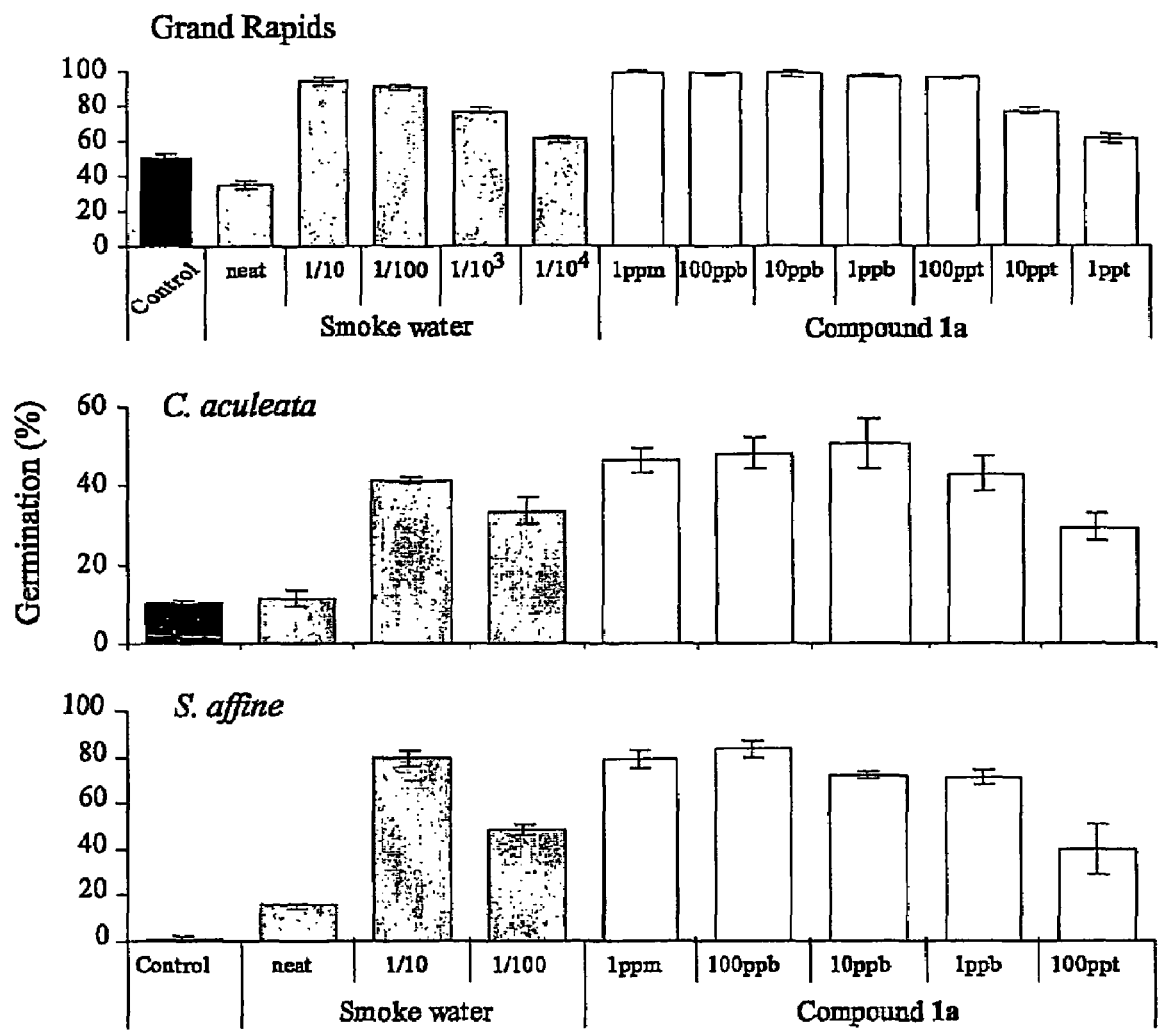
FIG. 2 shows a comparison of the germination promotion achieved with smoke water and compound 1a with Grand Rapids lettuce seed, *C. aculeata* and *S. affine*. Error bars represent standard errors of the mean (SEM).

Compound 1a was tested for promotion of germination using the two native species *Conostylis aculeata* (see Table 3 and FIG. 2) and *Stylidium affine* (see Table 4 and FIG. 2). A series of dilutions were tested and as a comparison, plant-derived smoke water (PDSW) was tested similarly to the Grand Rapids lettuce seed.

TABLE 3

*Conostylis aculeate* germination of compound 1a, compared to plant-derived smoke water (PDSW).

| Concentrations | Plant-derived SW | Compound 1a (1 mg/L) |
|---|---|---|
| Neat | 11.7 (2.1) | 46.3 (3.1) |
| 1/10 | 41.4 (0.9) | 48.2 (4.0) |
| 1/100 | 33.5 (3.3) | 50.6 (6.5) |
| 1/1000 | N/A | 43.0 (4.5) |
| 1/10000 | N/A | 29.4 (3.4) |

Note:
Values indicate mean germination percentages and parenthesis values indicate standard errors of the mean. Control (MP water) germination was 10.2% (0.8).

TABLE 4

*Stylidium affine* germination of synthetic compound 1a, compared to plant-derived smoke water (PDSW).

| Concentrations | Plant-derived SW | Compound 1a (1 mg/L) |
|---|---|---|
| Neat | 15.5 (1.1) | 79.0 (3.1) |
| 1/10 | 79.3 (3.8) | 83.4 (3.7) |
| 1/100 | 48.2 (2.3) | 71.8 (1.7) |
| 1/1000 | N/A | 70.9 (3.1) |
| 1/10000 | N/A | 39.9 (10.9) |

Note:
Values indicate mean germination percentages and parenthesis values indicate standard errors of the mean. Control (MP water) germination was 1.1% (1.1).

The germination results (Tables 3 and 4) show the synthetic compound 1a promotes the germination of the two test species, *Conostylis aculeata* and *Stylidium affine*, to an equivalent level to that observed with smoke water (1/10 dilution).

Further, tests in a range of test species have shown that compound 1a, at a range of concentrations (1 ppm to 100 ppt), promotes the germination of the test species at the same or greater level than that observed for smoke water (1/10 dilution). Furthermore, activity has been shown for concentrations of 100 ppt for each of the test species, illustrating the potent activity of this compound (i.e. active at <1 μg/L, $10^{-9}$ M). Testing of other plant species from Australia, South Africa and North America has further confirmed the germination promoting activity of 1a (see Table 5).

TABLE 5

Germination of other species in response to 1a and smoke water (SW).

| Plant Species | Control (water) | SW (1/10 dilution) | Compound 1a (10 ppb) |
|---|---|---|---|
| Australian | | | |
| *Brunonia australis* | 8.0 (±2.8) a | 22.0 (±7.6) b | 25.0 (±2.5) b |
| *Conostylis candicans* | 1.0 (±1.0) a | 49.0 (±3.4) b | 36.0 (±6.7) b |
| *Grevillea polybotrya* | 0.0 (±0.0) a | 1.0 (±1.0) b | 6.0 (±2.0) c |
| *Lawrencella davenportii* | 16.7 (±2.9) a | 46.4 (±0.7) b | 56.3 (±8.5) b |
| *Ozothamnus cordifolium* | 0.0 (±0.0) a | 10.0 (±2.6) b | 24.0 (±4.3) c |
| *Scaevola thesioides* | 2.0 (±2.0) a | 31.0 (±6.6) b | 17.0 (±5.5) b |
| *Verticordia densiflora* | 2.0 (±2.0) a | 14.9 (±1.1) b | 11.1 (±1.2) b |
| South African | | | |
| *Passerina vulgaris* | 0.0 (±0.0) a | 5.0 (±2.9) a | 10.0 (±4.1) b |
| *Rhodocoma arida* | 42.7 (±1.2) a | 82.7 (±3.6) c | *53.3 (±3.1) b |
| *Syncarpha vestita* | 33.8 (±2.4) a | 71.2 (±4.3) b | 77.5 (±6.3) b |
| North American | | | |
| *Camissonia californica* | 8.0 (±2.3) a | 82.7 (±1.3) b | 85.3 (±4.8) b |
| *Caulanthus heterophyllus* | 14.7 (±3.3) a | 96.0 (±1.1) b | 97.3 (±0.7) b |
| *Emmenanthe penduliflora* | 0.0 (±0.0) a | 72.0 (±5.0) b | 82.0 (±4.2) b |
| *Nicotiana attenuate* | 33.3 (±2.6) a | 47.3 (±0.9) b | **44.4 (±1.9) b |

Note:
The North American species and *L. davenportii* were tested on moist filter paper in petri dishes. All other species were tested in soil. Values represent mean germination percentages (%) and values in parenthesis indicate SEM. Different letters following values indicate significant difference ($p < 0.05$).
*Statistically significant with $p < 0.08$.
**Tested at 100 ppb.

Seed Vigour Results with Compound 1a

Figure 3:
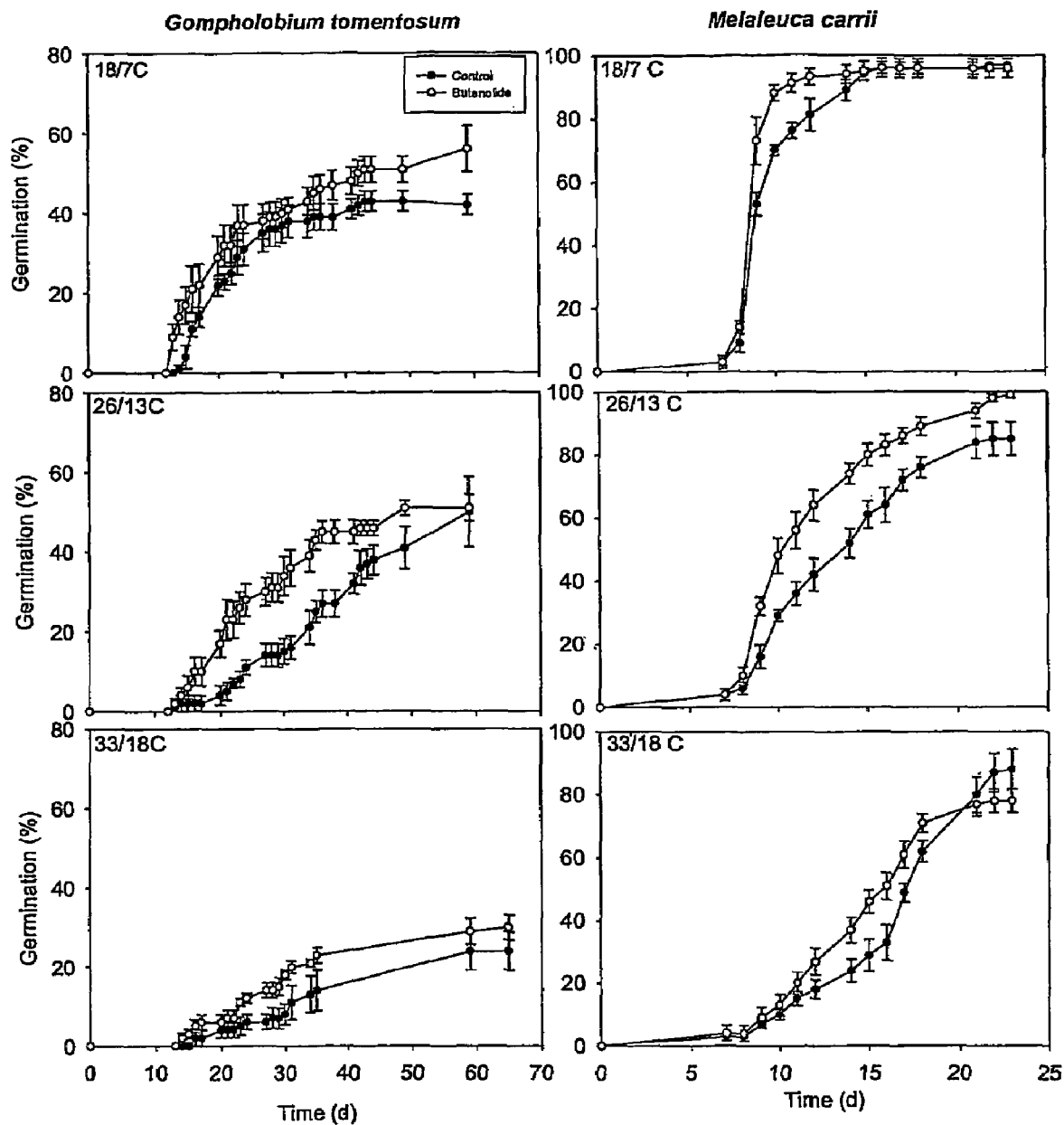
FIG. 3 shows the results of cumulative germination of *Gompholobium tomentosum* and *Melaleuca carrii* seeds demonstrating improved germination rate following treatment with compound 1a at 100 ppb. Values represent mean±standard error.
Figure 4:
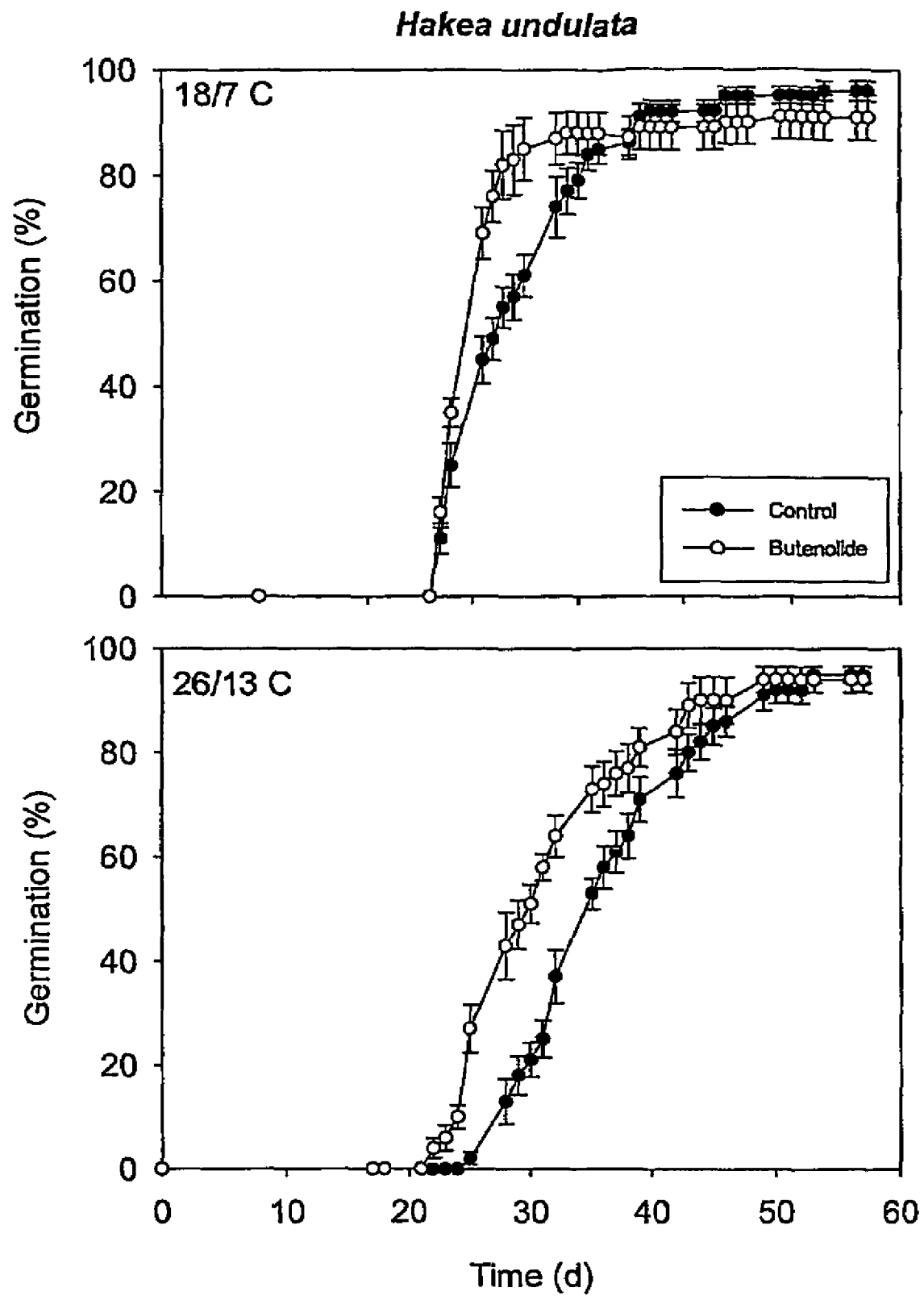
FIG. 4 shows cumulative germination of *Hakea undulata* seeds demonstrating improved germination rate following treatment with compound 1a at 100 ppb. Values represent mean±standard error.

Compound 1a was tested on seeds of a range of non-smoke requiring native species. The results demonstrate that compound 1a significantly increases the rate of germination over a range of temperatures (FIGS. 3 and 4). The increased germination rate is particularly enhanced at temperatures not normally favourable (warmer than optimal for germination).

Testing of the germination response to compound 1a using the vegetable species *Allium ampeloprasum* (leek) and *Petroselinium crispum* (parsley) seeds demonstrates compound 1a also enhances the germination percentage of vegetable seeds, particularly at warm temperatures (Table 6).

The improved germination at higher temperatures lessens uncertainty in propagation cycles and obviates the need for controlled temperature germination and associated costs.

TABLE 6

Germination of *Allium ampeloprasum* (leek) and *Petroselinium crispum* (parsley) seeds demonstrating improved germination at warm temperatures following treatment with 100 ppb compound 1a. Values represent mean ± standard error.

| | | Germination (%) | |
|---|---|---|---|
| Species | Temperature (° C.)* | Control | Compound 1a |
| Leek | 18/7 | 100.0 ± 0.0 a | 97.1 ± 0.9 a |
| | 26/13 | 91.0 ± 3.4 a | 92.0 ± 4.3 a |
| | 33/18 | 60.0 ± 3.6 a | 72.0 ± 6.3 b |
| Parsley | 18/7 | 32.0 ± 7.1 a | 27.0 ± 1.9 a |
| | 26/13 | 46.0 ± 6.2 a | 70 ± 5.6 b |
| | 33/18 | 11.0 ± 2.5 a | 29.0 ± 6.8 b |

*12/12 hr alternating temperature cycle.

Weed Germination Enhancement

The germination of a number of key weed species was tested against compound 1a. Table 7 demonstrates the germination improvement of three major agricultural/mining restoration weeds from three families (Poaceae, Brassicaceae and Polygonaceae) following exposure to compound 1a at 100 ppb. This finding implicates the compound and related compounds as a potential control measure for minimising weed impacts in agriculture, horticulture, restoration of mine sites and other restoration activities, amenity and home gardening, turf management by stimulation of the dormant weed seed bank followed by chemical control using known herbicide treatments.

TABLE 7

Effect of compound 1a on germination percentage of weed species. Values represent mean ± standard error.

| Species | Control | Compound 1a |
|---|---|---|
| *Avena fatua* (wild oats)* | 11.0 ± 1.1 a | 38.0 ± 4.3 b |
| *Brassica tournefortii* (wild turnip)* | 54.0 ± 5.0 a | 92.0 ± 2.8 b |
| *Acetosa vesicaria* (ruby dock)** | 2.0 ± 1.22 a | 30.0 ± 7.6 b |

*Agricultural weeds
**Weed of mining restoration areas

Germination Enhancement of Species Used in Amenity Agriculture

The germination of a range of species used in amenity horticulture and floriculture, demonstrate compound 1a at 100 ppb significantly increase germination (Table 8).

TABLE 8

Germination of a range of species employed in amenity, cut flower and restoration horticulture. Values represent mean ± standard error. Germination enhancement of species used in rangeland pasture systems

| Species | Control | Compound 1a |
|---|---|---|
| *Conostylis aculeata* | 10.2 ± 0.8 a | 48.2 ± 3.9 b |
| *Emmenanthe penduliflora* | 0.0 ± 0.0 a | 82.0 ± 4.2 b |
| *Stylidium affine* | 1.1 ± 1.1 a | 83.4 ± 3.7 b |
| *Passerina vulgaris* | 0.0 ± 0.0 a | 10.0 ± 4.1 b |
| *Rhodocoma arida* | 42.7 ± 1.2 a | 53.3 ± 3.1 b |
| *Syncarpha vestita* | 33.8 ± 2.4 a | 77.5 ± 6.3 b |

Testing of compound 1a on the Australian grass species *Microlaena stipoides* shows compound 1a at 100 ppb significantly increases germination of a species widely employed in native perennial pasture (Table 9).

TABLE 9

Germination of the perennial Australian grass species *Microlaena stipoides* following treatment with 100 ppb compound 1a. Values represent mean ± standard error.

| Species | Control | Compound 1a |
| --- | --- | --- |
| *Microlaena stipoides* | 48.3 ± 10.1 a | 78.3 ± 6.7 b |

Effective Delivery Systems for Compound 1a

Seed Coating

Seed coating technologies are routinely used in agriculture and horticulture.

Studies on *Emmenanthe penduilfora*, demonstrate that compound 1a may be effectively supplied to the seeds once incorporated into artificial seed coats (Table 10).

TABLE 10

Germination of coated seeds of *Emmenanthe penduliflora*. Seeds were coated using standard techniques, with and without compound 1a (100 ppb) added to the coating mix. Values represent mean ± standard error.

| Coat Type | Germination (%) |
| --- | --- |
| Film Coat | 1.33 ± 1.33 a |
| Film Coat + compound 1a | 23.5 ± 8.2 b |
| Polymer Coat + compound 1a | 26 ± 6.5 b |

Seed Priming

Seed priming is a technique employed in agricultural and horticultural industries to improve germination performance. Seed priming involves the controlled hydration of seeds, followed by re-drying prior to sowing.

Results demonstrate that seed priming is an effective method of delivering compound 1a. Seeds soaked for 24 hr in 100 ppb compound 1a, then re-dried prior to sowing retain the beneficial effects of compound 1a. Table 11 demonstrates the germination improvement of a range of Australian species following priming in 100 ppb compound 1a.

TABLE 11

Germination of a range of Australian species following 24 hr priming in 100 ppb compound 1a, re-drying and sowing. Values represent mean ± standard error.

| | Germination (%) | |
| --- | --- | --- |
| Species | Control | Compound 1a |
| *Borya sphaerocephala* | 1.3 ± 1.3 a | 13.3 ± 4.8 b |
| *Centrolepis aristate* | 41.3 ± 4.8 a | 88.0 ± 0.0 b |
| *Cherianthera preissiana* | 8.2 ± 2.7 a | 46.7 ± 4.8 b |
| *Opercularia vaginate* | 0.0 ± 0.0 a | 22.7 ± 7.4 b |
| *Phyllanthus calycinus* | 6.7 ± 3.5 a | 17.3 ± 1.3 b |

Figure 5:
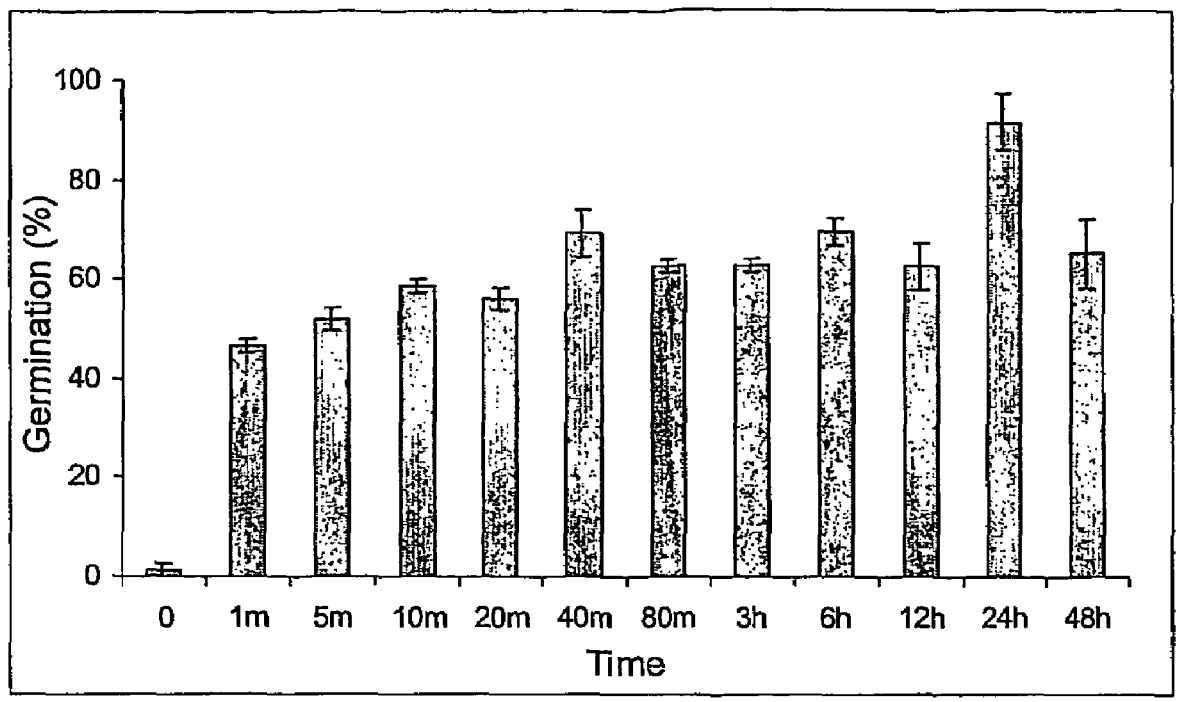
FIG. 5 shows germination of *Emmenanthe penduliflora* seeds following imbibing and re-drying for various time periods. Values represent mean±standard error.
Figure 6:
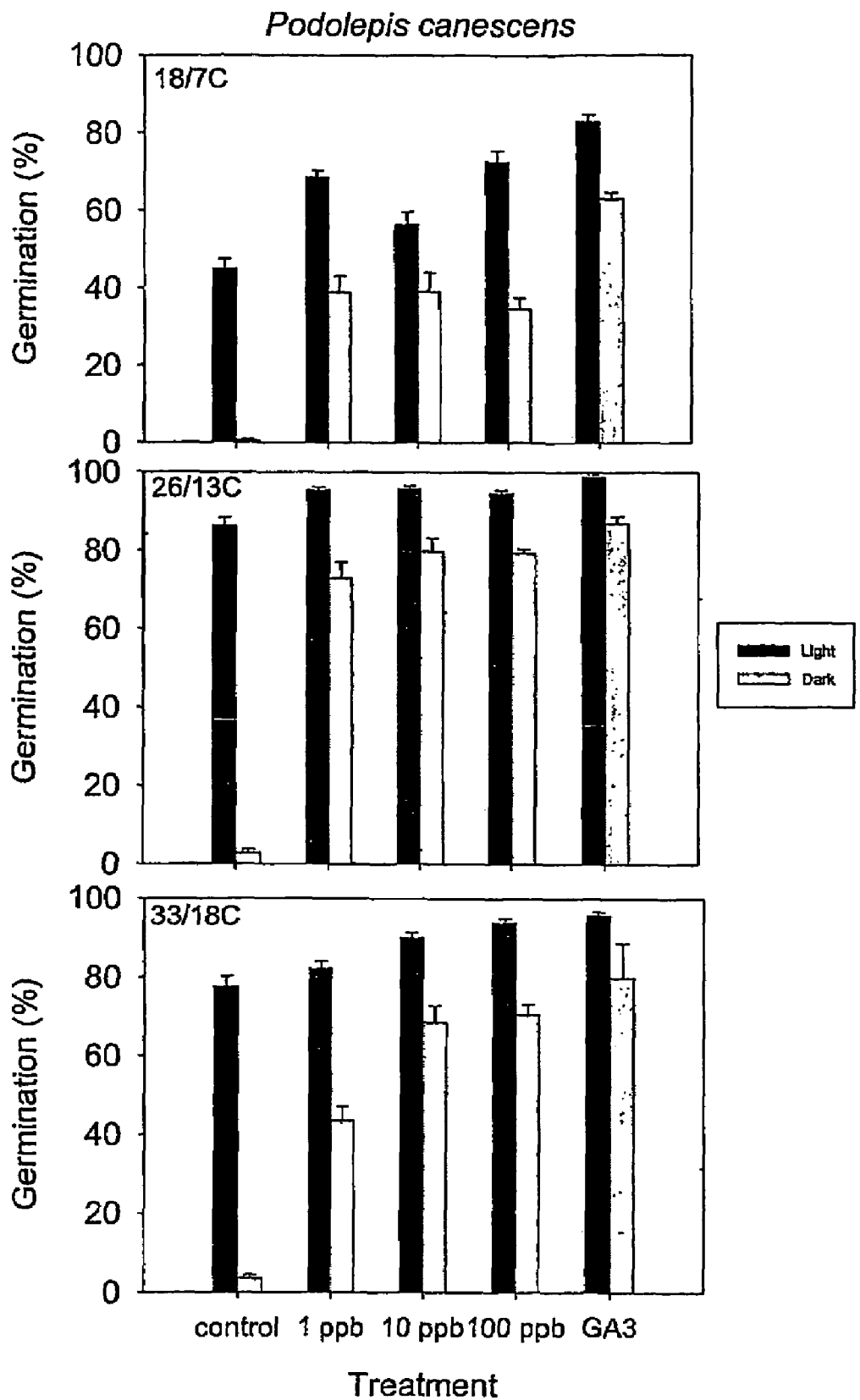
FIG. 6 shows germination of *Podolepis canescens* at a range of temperatures in the light or dark following treatment with 1, 10 or 100 ppb compound 1a or 1000 ppm gibberellic acid (GA3). Values represent mean±standard error.

Experiments were undertaken with *Emmenanthe penduliflora* seeds to determine the duration of priming in compound 1a required to induce a significant germination response. The results demonstrate that as little as 1 min priming in compound 1a is sufficient to induce germination promotion following re-drying then incubation (FIG. 5).

Compound 1a as a Replacement for the Other Dormancy Release Agents

Figure 9:
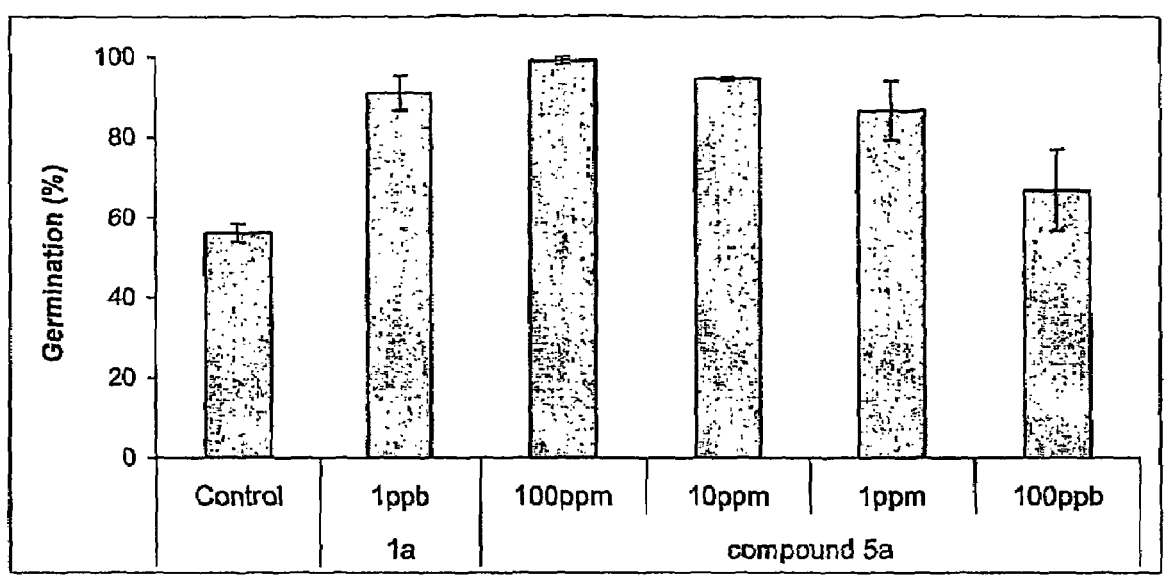
FIG. 9 shows a comparison of the germination promotion achieved with compound 5a compared with 1a (at 1 ppb) using Grand Rapids lettuce seed. Note compound 5a was tested at much higher concentrations than compared with the formula (1) analogues.

Results demonstrate that compound 1a can act as a replacement for other dormancy release/germination stimulating agents. Experiments with the light-requiring Australian species *Podolepis canescens* demonstrate compound 1a stimulates germination in the dark, in a manner similar to the well known germination stimulant gibberellic acid (FIG. 9).

Compound 1a can also replace the requirement for de-hulling of grass species, a practice generally required for maximum germination of grasses, but one that is technically difficult and time consuming. Experiments on the Australian grass species *Microlaena stipoides* demonstrate increased germination of intact seeds following treatment with 100 ppb compound 1a (Table 12).

TABLE 12

Effects of compound 1a on germination of intact and de-hulled *Microlaena stipoides* seeds. Values represent mean ± standard error.

| | Germination (%) | |
| --- | --- | --- |
| Seed Condition | Control | Compound 1a |
| Intact | 48.3 ± 10.3 a | 78.3 ± 6.3 b |
| De-hulled | 98.3 ± 1.6 a | 100 ± 0.0 a |

Compound 1a Stimulation of Germinations in Neutriceutically Important Plants

Germination of the neutriceutically important species *Echinacea angustifolia* is enhanced by the addition of compound 1a at 10 and 100 ppb (Table 13). The compound replaces the need for stratification of seed by storage at low temperatures (e.g. 5° C. for 4 weeks in moist wadding or moist paper towel). can be overcome not required by the use of compounds of the present invention.

TABLE 13

Effect of compound 1a on germination of *Echinacea angustifolia*. Values represent mean ± standard error.

| Species | Control | 10 ppb Compound 1a | 100 ppb Compound 1a |
| --- | --- | --- | --- |
| *Echinacea angustifolia* | 41.0 ± 6.0 a | 58.0 ± 5.5 b | 74.0 ± 4.0 b |

Reactivity of Compound 1a with Somatic Tissue

Results show that compound 1a at 10 ppb improved development and recovery of plants from somatic embryos. While 2,4-dichlorophenoxyacetic acid induces somatic embryogenesis, the compound 1a has no apparent effect on the induction phase. However, once somatic embryos are induced, the compound 1a significantly enhances root formation and plantlet maturation (Table 14). When somatic embryos were transferred to hormone-free medium, the compound 1a significantly improved plantlet recovery and regeneration.

TABLE 14

Effect of 2,4-dichlorophenoxyacetic acid on plantlet development from somatic embryos induced from shoot and coleoptile explants of *Baloskion tetraphyllum* after culturing for 20 days.

| Observation | Shoot Control | Shoot Compound 1a | Coleoptile Control | Coleoptile Compound 1a |
| --- | --- | --- | --- | --- |
| Frequency of shoot formation | 28.6 | 58.6 | 26.9 | 37.0 |
| Number of shoots | 2.3 | 7.8 | 2.8 | 4.5 |

Germination of Analogues with Grand Rapids Lettuce Seed.

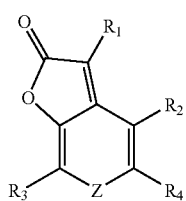

(formula 1)

The following compounds of formula 1 were prepared according to the above identified methods

TABLE 15

Structure of formula (1) analogues prepared.

| Compounds | Z | $R_1$ | $R_2$ | $R_3$ | $R_4$ |
| --- | --- | --- | --- | --- | --- |
| 1b | O | H | H | H | H |
| 1c | O | H | H | $CH_3$ | H |
| 1d | O | H | H | H | $CH_3$ |
| 1e | O | $CH_3$ | H | $CH_3$ | H |
| 1f | O | $CH_3$ | H | H | $CH_3$ |
| 1g | O | $CH_3$ | H | $CH_3$ | $CH_3$ |
| 1h | O | $CH_3$ | H | H | $CH_2OCH_3$ |
| 1i | O | $CH_3$ | Br | $CH_3$ | H |
| *1j | NH | $CH_3$ | H | H | H |
| 1k | N—$CH_3$ | $CH_3$ | H | H | H |

*exists in tautomeric form

Figure 7:
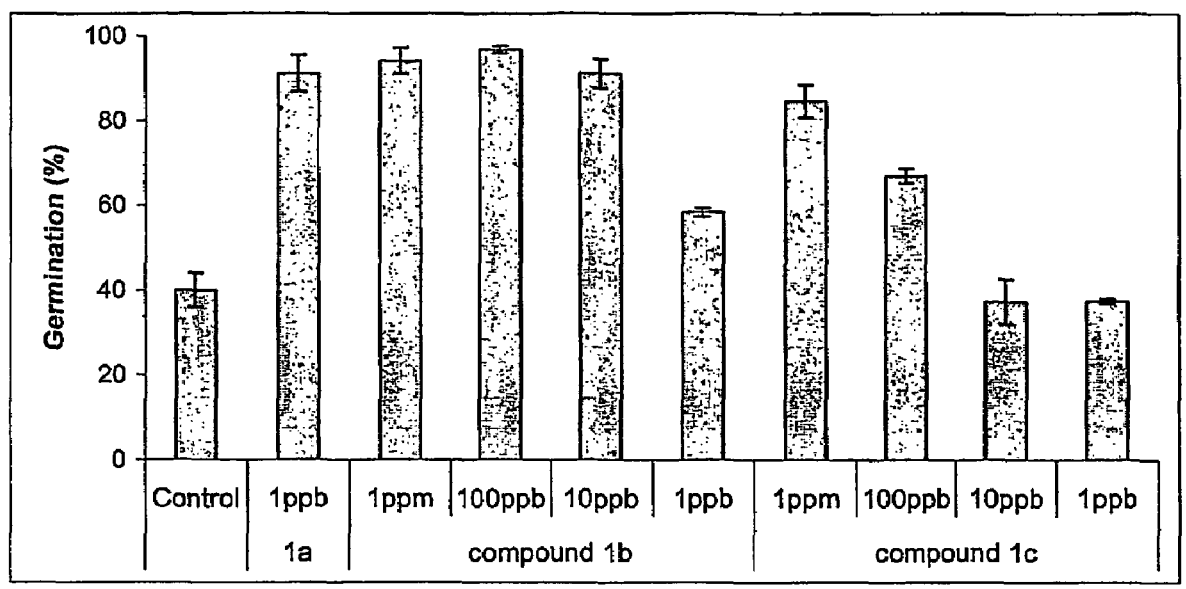
FIG. 7 shows a comparison of the germination promotion achieved with compounds 1b and 1c compared with 1a (at 1 ppb) using Grand Rapids lettuce seed.
Figure 8:
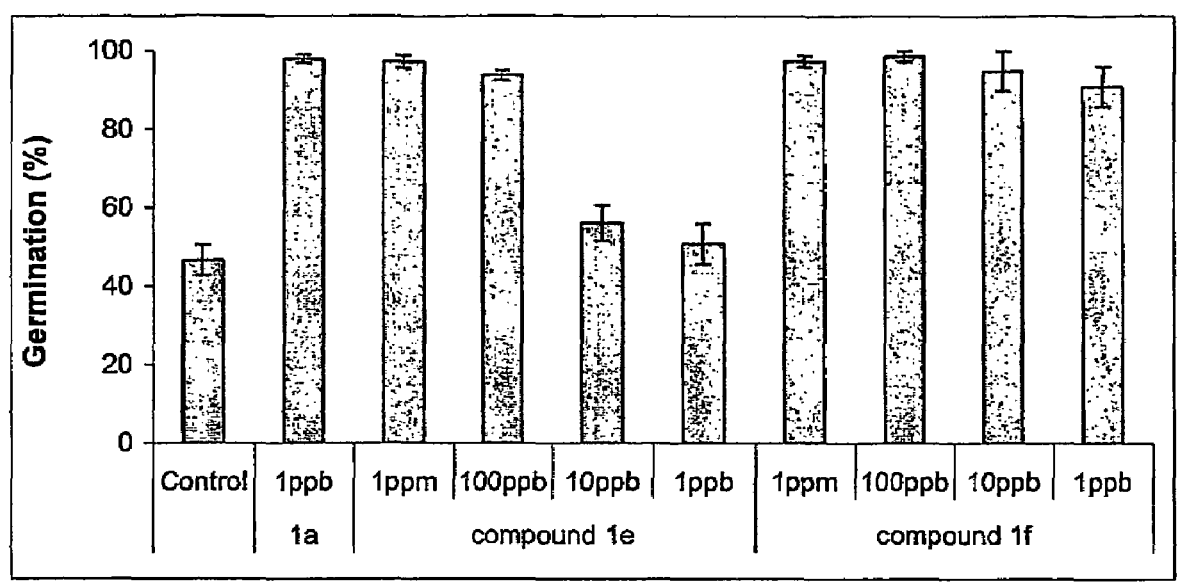
FIG. 8 shows a comparison of the germination promotion achieved with compounds 1e and 1f compared with 1a (at 1 ppb) using Grand Rapids lettuce seed.

The following Table 16 (FIGS. 7 and 8) depicts the germination activity of analogues tested at various concentrations (1 ppm to 1 ppb) with Grand Rapids lettuce seed in accordance with the above germination assay. MP water served as the control. Values in parenthesis indicate SEM.

TABLE 16

Germination of formula (1) analogues.

| No. | Control | 1 ppm | 100 ppb | 10 ppb | 1 ppb |
| --- | --- | --- | --- | --- | --- |
| 1b | 40.1 (±4.0) | 94.2 (±3.1) | 96.8 (±0.8) | 91.1 (±3.4) | 58.5 (±1.0) |
| 1c | 40.1 (±4.0) | 84.7 (±3.9) | 67.1 (±1.7) | 37.4 (±5.3) | 37.5 (±0.6) |
| 1d | 42.4 (±3.6) | 92.7 (±2.9) | 69.3 (±1.8) | 52.1 (±3.3) | 47.6 (±0.6) |
| 1e | 46.6 (±3.9) | 97.3 (±1.6) | 93.8 (±1.2) | 56.1 (±4.6) | 50.8 (±5.1) |
| 1f | 46.6 (±3.9) | 97.4 (±1.4) | 98.7 (±1.3) | 95.0 (±5.0) | 91.0 (±5.1) |
| 1g | 46.6 (±3.9) | 84.0 (±3.1) | 70.6 (±6.3) | 45.9 (±3.0) | 44.4 (±3.0) |
| 1h | 40.1 (±4.0) | 96.2 (±1.7) | 91.4 (±3.7) | 52.0 (±2.0) | 43.2 (±5.9) |
| 1i | 40.7 (±5.4) | 81.8 (±2.0) | 72.8 (±4.3) | 53.8 (±2.1) | 49.1 (±1.2) |
| 1j | 46.6 (±3.9) | 95.1 (±0.3) | 95.1 (±1.1) | 87.5 (±3.0) | 40.8 (±4.3) |
| 1k | 56.2 (±2.3) | 83.3 (±3.0) | 76.8 (±6.9) | 59.6 (±3.9) | 60.0 (±0.6) |

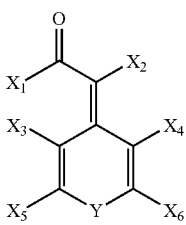

formula (5)

The following compounds of formula 5 were prepared

TABLE 17

Structure of formula (5) analogues prepared.

| Compounds | Y | $X_1$ | $X_2$ | $X_3$ and $X_4$ | $X_5$ and $X_6$ |
| --- | --- | --- | --- | --- | --- |
| 5a | O | OEt | H | H | H |
| 5b | O | OEt | $SCOCH_3$ | H | H |
| 5c | O | Ph | H | H | $CH_3$ |
| 5d | O | PhBr | H | H | $CH_3$ |

The following Table 18 (FIG 9) despicts the germination activity of formula (5) analogues tested at various concentrations (100 ppm to 100 ppb) with Grand Rapids lettuce seed in accordance with the above germination assay. MP water served as the control Values in parenthesis indicate SEM.

TABLE 18

| | | Germination of formula (5) analogues. | | | |
|---|---|---|---|---|---|
| No. | Control | 100 ppm | 10 ppm | 1 ppm | 100 ppb |
| 5a | 56.2 (±2.3) | 99.1 (±0.9) | 94.7 (±0.4) | 86.7 (±7.4) | 66.9 (±10.2) |
| 5b | 40.7 (±5.4) | *39.4 (±2.7) | 82.6 (±3.4) | 64.7 (±4.5) | 54.3 (±7.2) |
| 5c | 40.7 (±5.4) | 74.1 (±6.7) | 69.3 (±4.4) | 54.3 (±3.1) | 53.2 (±4.1) |
| 5d | 55.1 (±7.0) | *54.8 (±0.7) | 86.9 (±1.8) | 56.7 (±5.4) | 53.0 (±3.5) |

*inhibits germination at this concentration.

While an advantageous and preferred embodiment of the present invention has been selected and described as an illustration of the invention, it should be understood by those skilled in the art that changes and adaptations can be made therein without departing from the scope of the invention as defined.

REFERENCES

Baldwin, I. T.; Staszak-Kozinski, L.; Davidson, R. (1994). *Journal of Chemical Ecology*, 20, 2345-71.

Belsky, I.; Dodiuk, H.; Shvo, Y. (1974). *Journal of Organic Chemistry*, 39, 989-95.

Brown, N. A. C.; Van Staden, J. (1997). *Plant Growth Regulation*, 22, 115-24.

Dixon, K. W.; Roche, S.; Meney, K.; Von Perger, B. (1996). *Minerals and Energy Research Institute of Western Australia*, Research Report No. 174.

Dixon, K. W.; Roche, S.; Pate, J. S. (1995). *Oecologia*, 101, 185-92.

Ellis, B. L.; Duhme, A. K.; Hider, R. C.; Hossain, M. B.; Rizvi, S.; Van der Helm, D. (1996). *Journal of Medicinal Chemistry*, 39, 3659-70.

Hwang, D. R., Proctor, G. R., Driscoll, J. S. (1980). *Journal of Pharmaceutical Sciences*, 69, 1074-1076

Liu, Z. D., Piyamongkol, S., Liu, D. Y., Khodr, H. H., Lu, S. L., Hider, R. C. (2001) *Bioorganic and Medicinal Chemistry*, 9, 563-573

Looker, J. H., Prokop, R. J., Serbousek, W. E., Clifton, M. D. (1979). *Journal of Organic Chemistry*, 44, 3408-3410.

Ohkata, K.; Imagawa, M.; Akiba, K. (1986). *Heterocycles*, 24, 2817-20.

Rautenstrauch, V.; Megard, P.; Gamper, B.; Bourdin, B.; Walther, E. (1989). *Helvetica Chimica Acta*, 72, 811-24.

Scheeren, J. W.; Ooms, P. H. J.; Nivard, R. J. F. (1973). *Synthesis*, 149-51.

Van Staden, J.; Drewes, F. E.; Jäger, A. K. (1995). *South African Journal of Botany*, 61, 260-63.

Wu, J.; Zhu, Q.; Wang,. L.; Fathi, R.; Yang, Z. (2003). *Journal of Organic Chemistry*, 68, 670-73.

All publications, patents and published patent applications mentioned in the present specification, and references cited in said publications, are herein incorporated by reference. Various modifications and variations of the described methods and system of the invention will be apparent to those skilled in the art without departing from the scope and spirit of the invention.

We claim:
1. The compound of the formula (1):

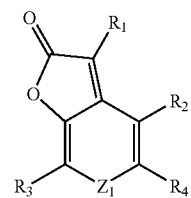

wherein;
$Z_1$ is O or $NR_5$;
$R_1, R_2, R_3$ and $R_4$ are each independently H, alkyl, hydroxy, hydroxyalkyl, alkoxy,
$COR_5$, $COOR_5$; and
$R_5$ is H or alkyl,
wherein the compound is provided in a state selected from the group consisting of; an enriched state, a substantially pure state, a substantially homogeneous state, an isolated state and a concentrated state.

2. The compound according to claim 1, wherein:
$Z_1$ is O;
$R_1$, $R_2$, $R_3$ and $R_4$ are each independently H, alkyl, hydroxy, hydroxyalkyl, alkoxy,
$COR_5$, $COOR_5$; and
$R_5$ is H or alkyl.

3. The compound according to claim 1, wherein:
$Z_1$ is O;
$R_1$, $R_2$, $R_3$ and $R_4$ are each independently H or alkyl.

4. The compound according to claim 1, wherein said alkyl and alkoxy groups are $C_1$-$C_4$, and said alkenyl and alkynyl groups are $C_2$-$C_4$.

5. The compound according to claim 1, wherein the compound of the invention is selected from: 3-methyl-2H-furo[2,3-c]pyran-2-one (where $R_1$ is $CH_3$, and $R_2$, $R_3$ and $R_4$ are H), 2H-furo[2,3-c]pyran-2-one (where $R_1$, $R_2$, $R_3$ and $R_4$ are H), 7-methyl-2H-furo[2,3-c]pyran-2-one (where $R_1$, $R_2$, and $R_4$ are H, and $R_3$ is $CH_3$), 5-methyl-2H-furo[2,3-c]pyran-2-one (where $R_1$, $R_2$ and $R_3$ are H, and $R_4$ is $CH_3$), 3,7-dimethyl-2H-furo[2,3-c]pyran-2-one (where $R_1$ and $R_3$ are $CH_3$, and $R_2$ and $R_4$ are H), 3,5-dimethyl-2H-furo[2,3-c]pyran-2-one (where $R_1$ and $R_4$ are $CH_3$, $R_2$, and $R_3$ is H), 3,5,7-trimethyl-2H-furo[2,3-c]pyran-2-one (where $R_1$, $R_3$ and $R_4$ are $CH_3$, and $R_2$ is H), 3-methylfuro[2,3-c]pyridin-2(3H)-one (where Z is NH, $R_1$ is $CH_3$, $R_2$, $R_3$ and $R_4$ is H), 3,6-dimethylfuro[2,3-c]pyridin-2(6H)-one (where Z is N-$CH_3$, $R_1$ is $CH_3$, $R_2$, $R_3$ and $R_4$ are H).

6. The compound according to claim 1, wherein the compound contains one or more asymmetric centres, and wherein said compound may exist as enantiomers or diastereomers.

7. The compound according to claim 1, wherein the compound exists in tautomeric forms.

8. The compound according to claim 1, wherein the halogen substituent is selected from the group consisting of fluoro, chloro, bromo and iodo.

9. The compound according to claim 1, wherein the alkyl substituent has three or more carbon atoms and wherein the alkyl substituent is either straight chained or branched.

10. The compound according to claim 1, wherein the alkenyl or alkynyl substituents have four or more carbon atoms and wherein the alkoxy substituent has more than three carbon atoms.

11. The compound according to claim 1, wherein any of the alkyl, alkenyl, alkynyl, alkoxy, phenyl, phenyloxy substituents are optionally substituted with one or more halogens.

12. The compound according to claim 1, wherein any of the phenyl, phenyloxy, benzyl, benzyloxy substituents are optionally substituted with one or more grounds independently selected from the group consisting of alkyl, alkenyl, alkynyl, hydroxy, alkoxy and hydroxyalkyl groups.

13. The compound according to claim 12, wherein said compound is selected from the group consisting of: 3-methyl-2H-furo[2,3-c]pyran-2-one, 2H-furo[2,3-c]pyran-2-one, 7-methyl-2H-furo[2,3-c]pyran-2-one, 5-methyl-2H-furo[2,3-c]pyran-2-one, 3,7-dimethyl-2H-furo[2,3-c]pyran-2-one, 3,5-dimethyl-2H-furo[2,3-c]pyran-2-one, 3,5,7-trimethyl-2H-furo[2,3-c]pyran-2-one, 3-methylfuro[2,3-c]pyridin-2(3H)-one or 3,6-dimethylfuro[2,3-c]pyridin-2(6H)-one.

14. The compound according to claim 1, wherein the compound includes radio-labelled derivatives which are suitable for biological studies.

15. A method for the preparation of the compound of formula (1), the method comprising the step of: treating a compound having the formula (2):

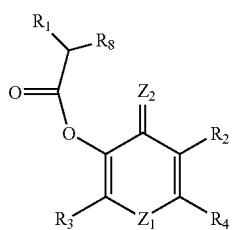

wherein;
$Z_1$ is O, S, or $NR_5$;
$Z_2$ is O or S;
$R_8$ is H, Cl, Br, or $PO(OEt)_2$
$R_1, R_2, R_3$ and $R_4$ are each independently H, alkyl, alkenyl, alkynyl, phenyl, benzyl, hydroxy, hydroxyalkyl, alkoxy, phenyloxy, benzyloxy, CN, $COR_6$, $COOR_6$, halogen, $NR_6R_7$ or $NO_2$; and
$R_5, R_6$ and $R_7$ are each independently H or alkyl,
with acetic anhydride or propionic anhydride.

16. A method according to claim 15, wherein:
Z is O or $NR_5$;
$R_1, R_2, R_3$ and $R_4$ are each independently H, alkyl, alkenyl, alkynyl, phenyl, benzyl, hydroxy, hydroxyalkyl, alkoxy, phenyloxy, benzyloxy, $COR_6$, $COOR_6$, halogen, $NR_6R_7$ or $NO_2$;
$R_5, R_6$ and $R_7$ are each independently H or alkyl; and
$R_8$ is Cl or Br.

17. A method for the preparation of the compound of formula (1), the method comprising the step of: heating a compound of formula (2) under reflux using a suitable solvent.

18. A method for the preparation of the compound of formula (1), the method comprising the step of: treating a compound of formula (2) with a base in a suitable solvent.

19. A method for the preparation of the compound of formula (1), the method comprising the step of: heating a compound of formula (2) under reflux using a suitable solvent followed by treatment with a strong base in a suitable solvent in the presence or absence of a desulfurising agent.

20. A method for the preparation of the compound of formula (1), the method comprising the step of: producing the compound of formula (2) by the step of treatment of a compound having the formula (3):

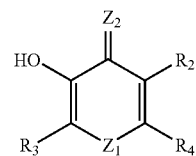

wherein;
$Z_1$ is O, S or $NR_5$;
$Z_2$ is O or S;
$R_2, R_3$ and $R_4$ are each independently H, alkyl, alkenyl, alkynyl, phenyl, benzyl, hydroxy, hydroxyalkyl, alkoxy, phenyloxy, benzyloxy, CN, $COR_6$, $COOR_6$, halogen, $NR_6R_7$ or $NO_2$; and
$R_5, R_6$ and $R_7$ are each independently H or alkyl;
with a compound having the formula (3a):

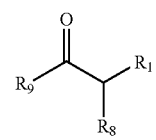

wherein;
$R_1$ is H, alkyl, alkenyl, alkynyl, phenyl, benzyl, hydroxy, hydroxyalkyl, alkoxy, phenyloxy, benzyloxy, CN, $COR_6$, $COOR_6$, halogen, $NR_6R_7$ or $NO_2$;
$R_6$ and $R_7$ are each independently H or alkyl;
$R_8$ is H, Cl, Br, or $PO(OEt)_2$; and
$R_9$ is Cl or Br.

21. A method for the preparation of the compound of formula (1), the method comprising the step of: producing the compound of formula (2) by the step of treatment of a compound having the formula (3'):

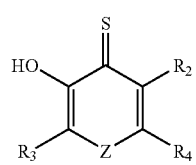

wherein;

Z is O or NR$_5$;

R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$ or NO$_2$; and R$_5$, R$_6$ and R$_7$ are each independently H or alkyl;

with a compound having the formula (3a'):

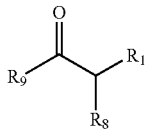

3a' wherein;

R$_1$ is H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$ or NO$_2$;

R$_6$, and R$_7$ are each independently H or alkyl;

R$_8$ is H, Cl or Br; and

R$_9$ is Cl or Br.

22. The method according to claim 20 or 21, wherein compound (2) is 4-thioxo-4H-pyran-3-yl 2-chloropropanoate, compound (3) is 3-hydroxy-4H-pyran-4-thione and is treated with 2-chloropropionyl chloride.

23. A method for the preparation of a compound of formula (1), the method comprising the step of: of producing a compound of formula (3) by the step of treatment of a compound of formula (4):

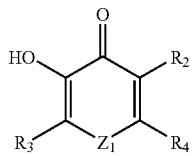

4 wherein;

Z$_1$ is O, S or NR$_5$;

R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$, NO$_2$; and R$_5$, R$_6$ and R$_7$ are each independently H or alkyl, with phosphorous pentasulphide.

24. A method for the preparation of a compound of formula (1), the method comprising the step of: of producing a compound of formula (3) by the step of treatment of a compound of formula (4'):

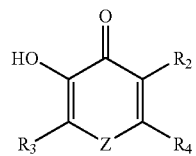

4' wherein;

Z$_1$ is O or NR$_5$;

R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR$_6$, halogen, NR$_6$R$_7$, NO$_2$; and R$_5$, R$_6$ and R$_7$ are each independently H or alkyl, with phosphorous pentasulphide.

25. The method according to claim 23 or 24, wherein compound (3) is 3-hydroxy-4H-pyran-4-thione and compound (4) is 3-hydroxy-4H-pyran-4-one (pyromeconic acid).

26. A compound selected from 5-methoxymethyl-3-methyl-2H-furo[2,3-c]pyran-2-one or 4-bromo-3,7-dimethyl-2H-furo[2,3-c]pyran-2-one.

* * * * *